US008299101B2

(12) United States Patent
Cid-Núñez et al.

(10) Patent No.: US 8,299,101 B2
(45) Date of Patent: Oct. 30, 2012

(54) 1,4-DISUBSTITUTED 3-CYANO-PYRIDONE DERIVATIVES AND THEIR USE AS POSITIVE MGLUR2-RECEPTOR MODULATORS

(75) Inventors: José Maria Cid-Núñez, Toledo (ES); Andrés Avelino Trabanco-Suárez, Olias del Ray (ES); Gregor James MacDonald, Zoersel (BE); Guillaume Albert Jacques Duvey, Saint Julien en Genevois (FR); Robert Johannes Lütjens, Geneva (CH)

(73) Assignees: Janssen Pharmaceuticals, Inc., Titusville, NJ (US); Addex Pharma S.A., Geneva (CH)

( * ) Notice: Subject to any disclaimer, the term of this patent is extended or adjusted under 35 U.S.C. 154(b) by 345 days.

(21) Appl. No.: 12/529,555

(22) PCT Filed: Mar. 7, 2008

(86) PCT No.: PCT/EP2008/052767
§ 371 (c)(1),
(2), (4) Date: Sep. 2, 2009

(87) PCT Pub. No.: WO2008/107480
PCT Pub. Date: Sep. 12, 2008

(65) Prior Publication Data
US 2010/0099715 A1 Apr. 22, 2010

(30) Foreign Application Priority Data

Mar. 7, 2007 (EP) ..................................... 07103654
Mar. 15, 2007 (EP) .................. PCT/EP2007/052442
Sep. 14, 2007 (EP) ..................................... 07116402

(51) Int. Cl.
*A61K 31/443* (2006.01)
*C07D 401/04* (2006.01)
(52) U.S. Cl. ....................... 514/344; 546/261
(58) Field of Classification Search .................. 514/344; 546/261
See application file for complete search history.

(56) References Cited

U.S. PATENT DOCUMENTS

| 4,066,651 A | 1/1978 | Brittain et al. |
| 4,358,453 A | 11/1982 | Bristol et al. |
| 4,550,166 A | 10/1985 | Moran et al. |
| 5,032,602 A | 7/1991 | Fey et al. |
| 5,236,917 A | 8/1993 | Dunlap et al. |
| 5,356,911 A | 10/1994 | Muller-Gliemann et al. |
| 5,371,074 A | 12/1994 | Dunlap et al. |
| 5,374,513 A | 12/1994 | Ohzeki et al. |
| 5,498,774 A | 3/1996 | Mitsudera et al. |
| 5,596,012 A | 1/1997 | Dunlap et al. |
| 5,650,422 A | 7/1997 | Dunlap et al. |
| 5,874,432 A | 2/1999 | Dunlap et al. |
| 5,948,911 A | 9/1999 | Pamukcu et al. |
| 6,110,920 A | 8/2000 | Rochus et al. |
| 6,133,271 A | 10/2000 | Pamukcu et al. |
| 6,607,563 B2 | 8/2003 | Ohashi et al. |
| 7,456,289 B2 | 11/2008 | Hsieh et al. |
| 7,572,807 B2 | 8/2009 | Li et al. |
| 7,579,360 B2 | 8/2009 | Li et al. |
| 2003/0171380 A1 | 9/2003 | Arvanitis et al. |
| 2005/0113283 A1 | 5/2005 | Solow-Cordero et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2009/0031422 A1 | 1/2009 | Aaron et al. |
| 2009/0124609 A1 | 5/2009 | Albrecht et al. |
| 2009/0124612 A1 | 5/2009 | Albrecht et al. |
| 2009/0203668 A1 | 8/2009 | Li et al. |
| 2009/0318436 A1 | 12/2009 | Albrecht et al. |
| 2010/0063092 A1 | 3/2010 | Cid-Nunez et al. |
| 2010/0087487 A1 | 4/2010 | Cid-Nunez et al. |
| 2010/0166655 A1* | 7/2010 | Imogai et al. .................. 424/9.1 |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2011/0275624 A1 | 11/2011 | Cid-Nunez et al. |
| 2011/0306642 A1 | 12/2011 | Cid-Nunez et al. |

FOREIGN PATENT DOCUMENTS

| CA | 1019323 | 10/1977 |
| CN | 2390948 | 12/2000 |
| CN | 1842532 | 10/2006 |
| CN | 102002040 | 4/2011 |
| EP | 154190 | 9/1985 |

(Continued)

OTHER PUBLICATIONS

Seddon "Psudopolymorph . . . " Crystal growth & design 4(6) p. 1087 (2004) (two pages from internet).* Braga et al. "Making crystals from . . . " J. Roy. Soc. Chem. Chem. Commun. p. 3635-3645 (2005).*
Allosteric regulation, Wikipedia, p. 1-4 (2012).*
Christopoulos "Allostric binding . . . " Nature Rev. March vol. 1, p. 199-210 (2002).*
Benneyworth et al., "A Selective Positive Allosteric Modulator of Metabotropic Glutamate Receptor Subtype 2 Blocks a Hallucinogenic Drug Model of Psychosis," Mol. Pharmacol., 2007, 72, 477-484.
International Search Report and Combination Written Opinion of the International Searching Authority mailed Jul. 2, 2008 in re PCT/EP2008/052767, filed Mar. 7, 2008.

(Continued)

Primary Examiner — Celia Chang
(74) Attorney, Agent, or Firm — Gardner Groff Greenwald & Villanueva, PC

(57) ABSTRACT

The present invention relates to novel compounds, in particular novel pyridinone derivatives according to Formula (I) including any stereochemically isomeric form thereof, or a pharmaceutically acceptable salt thereof or a solvate thereof, wherein all radicals are defined in the application and claims. The compounds according to the invention are positive allosteric modulators of metabotropic glutamate receptors subtype 2 ("mGluR2") which are useful for the treatment or prevention of neurological and psychiatric disorders associated with glutamate dysfunction and diseases in which the mGluR2 subtype of metabotropic receptors is involved. In particular, such diseases are central nervous system disorders selected from the group of anxiety, schizophrenia, migraine, depression, and epilepsy. The invention is also directed to pharmaceutical compositions and processes to prepare such compounds and such compositions, as well as to the use of such compounds for the prevention and treatment of such diseases in which mGluR2 is involved.

16 Claims, No Drawings

FOREIGN PATENT DOCUMENTS

| | | |
|---|---|---|
| EP | 0373423 | 6/1989 |
| EP | 0430385 | 6/1991 |
| EP | 447118 | 9/1991 |
| EP | 0452002 | 10/1991 |
| EP | 10482939 | 4/1992 |
| EP | 0542059 | 5/1993 |
| EP | 1006112 | 6/2000 |
| EP | 1764099 | 3/2007 |
| GB | 1502312 | 3/1978 |
| JP | H02503317 | 10/1991 |
| JP | 2000072751 | 3/2000 |
| JP | 2002308882 | 10/2002 |
| JP | 2008509714 | 4/2008 |
| RU | 12143433 | 12/1999 |
| SU | 1796625 | 2/1993 |
| WO | 9504733 | 2/1995 |
| WO | 9511233 | 4/1995 |
| WO | 9710238 | 3/1997 |
| WO | 9721701 | 6/1997 |
| WO | 9811075 | 3/1998 |
| WO | 9817668 | 4/1998 |
| WO | 9824780 | 6/1998 |
| WO | 9832762 | 7/1998 |
| WO | 9962908 | 12/1999 |
| WO | 0003990 | 1/2000 |
| WO | 0034244 | 6/2000 |
| WO | 0129025 | 4/2001 |
| WO | 0132632 | 5/2001 |
| WO | 2001056990 | 8/2001 |
| WO | 0168097 | 9/2001 |
| WO | 0170731 | 9/2001 |
| WO | 0183481 | 11/2001 |
| WO | 0196308 | 12/2001 |
| WO | 0210807 | 2/2002 |
| WO | 0212236 | 2/2002 |
| WO | 0222598 | 3/2002 |
| WO | 0228837 | 4/2002 |
| WO | 02074025 | 9/2002 |
| WO | 02090333 | 11/2002 |
| WO | 02096318 | 12/2002 |
| WO | 02096363 | 12/2002 |
| WO | 03029209 | 4/2003 |
| WO | 03044021 | 5/2003 |
| WO | 03059884 | 7/2003 |
| WO | 03062392 | 7/2003 |
| WO | 03065994 | 8/2003 |
| WO | 03068230 | 8/2003 |
| WO | 03068750 | 8/2003 |
| WO | 2004017950 | 3/2004 |
| WO | 2004018386 | 3/2004 |
| WO | 2004021984 | 3/2004 |
| WO | 2005021552 | 3/2004 |
| WO | 2004031189 | 4/2004 |
| WO | 2004072025 | 8/2004 |
| WO | 2004078175 | 9/2004 |
| WO | 2004092123 | 10/2004 |
| WO | 2004092135 | 10/2004 |
| WO | 2005002585 | 1/2005 |
| WO | 2005028445 | 3/2005 |
| WO | 2005040337 | 5/2005 |
| WO | 2005080356 | 9/2005 |
| WO | 2005097052 | 10/2005 |
| WO | 2006012622 | 2/2006 |
| WO | 2006014918 | 2/2006 |
| WO | 2006015158 | 2/2006 |
| WO | 2006015737 | 2/2006 |
| WO | 2006018727 | 2/2006 |
| WO | 2006020879 | 2/2006 |
| WO | 2006030031 | 3/2006 |
| WO | 2006030032 | 3/2006 |
| WO | 2006074041 | 7/2006 |
| WO | 2007031558 | 3/2007 |
| WO | 2007039439 | 4/2007 |
| WO | 2007059257 | 5/2007 |
| WO | 2007027669 | 8/2007 |
| WO | 2007103760 | 9/2007 |
| WO | 2007104783 | 9/2007 |
| WO | 2007113276 | 10/2007 |
| WO | 2007122258 | 11/2007 |
| WO | 2007135527 | 11/2007 |
| WO | 2007135529 | 11/2007 |
| WO | 2008006540 | 1/2008 |
| WO | 2008008539 | 1/2008 |
| WO | 2008012622 | 1/2008 |
| WO | 2008045393 | 4/2008 |
| WO | 2008051197 | 5/2008 |
| WO | 2008057855 | 5/2008 |
| WO | 2008076225 | 6/2008 |
| WO | 2008078091 | 7/2008 |
| WO | 2008078100 | 7/2008 |
| WO | 2008107125 | 9/2008 |
| WO | 2008107479 | 9/2008 |
| WO | 2008107480 | 9/2008 |
| WO | 2008107481 | 9/2008 |
| WO | 2008124085 | 10/2008 |
| WO | 2009033702 | 3/2009 |
| WO | 2009033703 | 3/2009 |
| WO | 2009033704 | 3/2009 |
| WO | 2009045753 | 4/2009 |
| WO | 2009062676 | 5/2009 |
| WO | 2009091374 | 7/2009 |
| WO | 2009124609 | 10/2009 |
| WO | 2010022076 | 2/2010 |
| WO | 2010022081 | 2/2010 |
| WO | 2010043396 | 4/2010 |
| WO | 2010063054 | 6/2010 |
| WO | 2010060589 | 7/2010 |
| WO | 2010089303 | 8/2010 |
| WO | 2010117926 | 10/2010 |
| WO | 2010025890 | 11/2010 |
| WO | 2010130422 | 11/2010 |
| WO | 2010130423 | 11/2010 |
| WO | 2010130424 | 11/2010 |

OTHER PUBLICATIONS

International Search Report and Combination Written Opinion of the International Searching Authority mailed Jun. 10, 2008 in re PCT/EP2008/052768, filed Mar. 7, 2008.

International Search Report and Combination Written Opinion of the International Searching Authority mailed Jun. 10, 2008 in re PCT/EP2008/052766, filed Mar. 7, 2008.

Eisa et al., "Synthesis of some novel tetrazole derivatives as potential antimicrobial agents," Pakistan J. of Scientific and Industrial Res, vol. 33, 1990, pp. 417-420.

Ruggero Galici, Carrie K. Jones, Kamondanai Hemstapat, Yi Nong, Nicholas G. Echemendia, Lilly C. Williams, Tomas de Paulis, and P. Jeffrey Conn, "Biphenyl-indanone A, a Positive Allosteric Modulator of the Metabotropic Glutamate Receptor Subtype 2, Has Antipsychotic- and Anxiolytic-Like Effects in Mice," JPET 318:173-185 2006.

The Synthesis of Perloline, 6-(3,4-Dimethoxyphenyl)-5-hydroxy-5,6-dihydrobenzo[c][2,7]napththyridin-4(3H)-one, Prager et al., Aust. J. Chem., 1983, 36, 1441-53.

A 'Biogenetic Like' Synthesis of Perloline, 6-(3,4-Dimethoxyphenyl)-5-hydroxy-5,6-dihydrobenzo[c][2,7]naphthyridin-4 (3H)-one, Duong, et al., Aust. J. Chem., 1983, 36, 1431-40.

Ring Transformation of Uracils to 3-Pyridones. Hydrolysis of 6-(2-Dimethylaminovinyl) Uracils, Senda et al., Heterocycles, vol. 9, No. 6, 1978 (6 pages).

Synthese von 3-Cyan-6-methyl-4-pyridyl-und 3-cyan-4-methyl-6-pyridyl-pyrid-2(1H)-onen und -thionen, Hanfeld, et al., Pharmazie 43 (1988), H.11, 762-764.

Studies with Polyfunctionally Substituted Heteroaromatics: New Routes for the Synthesis of Polyfunctionally Substituted Pyridines and 1,2,4-Triazolo[1,5-a]pyridines, Al-Omran, et al., Heteroatom. Chemistry, vol. 6, No. 6, 1995, 545-551.

Diels-Alder Reactions of the Heterodiene System in 2(1H)-Pyrazinones, Tutonda, et al., Tetrahedron Letters, vol. 27, No. 22, pp. 2509-2512, 1986.

Cycloadditions of Cyanoketenes to Cinnamylideneamines and Benzylideneamines. Synthetic Scope, Stereochemistry, and Mechanism, Moore, et al., J. Org. Chem, 1985, 50, 4231-4238.

Reactions of Some 4-Methylene-4H-pyran Derivatives with Primary and Secondary Amines, VanAllan, et al., Journal of Heterocyclic Chemistry, vol. 7,Jun. 1970, 495-507.
A One-Step Preparation of Functionalized 3-Cyano-2-Pyridones, Jain, et al., Tetrahedron Letters, vol. 36, No. 19, pp. 3307-3310, 1995.
A new Synthetic Approach to the C-D Ring Portion of Streptonigrin Analogues, Kilama, et al., Journal of Heterocyclic Chemistry, vol. 27, Jul.-Aug. 1990, 1437-1440.
A Convenient Method for the Preparation of 2-Pyridone Derivatives, Kambe et al., 1977, vol. 12, pp. 841-842.
Torp-Ziegler Cyclization in the Synthesis of 3-Amino-4-Cyanopyrrole Derivatives, Ryndina, et al., Chemistry of Heterocyclic Compounds, vol. 36, No. 12, 2000, pp. 1409-1420.
Derivatives of 2-Pyridone, Wenner, et al., Journal of Organic Chemistry, 1946, vol. 11, pp. 751-759.
Alkylations at the Methyl or alpha-Methylene Group of 6- or 4-Alkyl-3-cyano-2(1)-pyridones through Dianions, Boatman, et al., Journal of Organic Chemistry, 1965, vol. 30 Pt 11, pp. 3593-3597.
Chemical Abstract, Yalyaheva et al., Heterocycles, p. 687, vol. 107, 1987.
Chemical Abstracts, Ershov et al., 1985, vol. 103, Pt 21, pp. 678.
Therapeutic potential of non-competitive, subtype-selective metabotropic glutamate receptor ligands, V. Mutel, Expert Opin. Ther. Patents (2002), 12 (12) p. 1845-1852.
Regulation of Neurotransmitter Release by Metabotropic Glutamate Receptors, Cartmell et al., J. Neurochem., p. 889-907, vol. 75, No. 3, 2000.
The selective group mGlu2/3 receptor agonist LY379268 suppresses REM sleep and fast EEG in the rat, Feinberg et al., Pharmacology, Biochemistry and Behavior 73 (2002) 467-474.
A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, Galici et al., J of Pharmacology and Experimental Therapeutics, p. 1181-1187, vol. 315, No. 3, (2005).
Activation of Group II Metabotropic Glutamate Receptors Inhibits Synaptic Excitation of the Subsantia Nigra Pars Reticulata, Bradley et al., J. of Neuroscience, May 1, 2000, 20(9):3085-3094.
Anxiolytic effects of a novel group II metabotropic glutamate receptor agonist (LY354740) in the fear-potentiated startle paradigm in humans, Grillon, et al., Psychopharmacology (2003) 168:446-454.
Anxiolytic and Side-Effect Profile of LY354740: A Potent, Highly Selective, Orally Active Agonist for Group II Metabotropic Glutamate Receptors, Helton et al., J. of Pharmacology and Experimental Therapeutics, p. 651-660, vol. 284, No. 2, 1997.
Excited by Glutamate, Science, p. 1866-1868, vol. 300, Jun. 20, 2003.
Benzazoles as allosteric potentiators of metabotropic glutamate receptor 2 (mGluR2): Efficacy in an animal model for schizophrenia, Govek et al., Bioorg. Med. Chem Lett. 15 (2005) 4068-4072.
Metabotropic glutamate 2 receptor potentiators: receptor modulation, frequency-dependent synaptic activity, and efficacy in preclinical anxiety and psychosis model(s), Johnson et al., Psychopharmacology (2005) 179: 271-283.
Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylmethyl-amine, Johnson et al., J. Med. Chem. 2003, 46, 3189-3192.
Effects of metabotropic glutamate2/3 receptor agonist (LY544344/LY354740) on panic anxiety induced by cholecystokinin tetrapeptide in health humans: preliminary results, Kellner et al., Psychopharmacology (2005) 179: 310-315.
Allosteric modulators of metabotropic glutamate receptors: lessons learnt from mGlu1, mGlu2 and mGlu5 potentiators and antagonists, Johnson et al., Biochemical Society Transactions (2004) vol. 32, part 5, 881-887.
Selective, Non-Amino Acid Allosteric mGlu2 Receptor Potentiators Inhibit Dural Plasma Protein Extravasation; A Potential Role in the Treatment of Migraine, Johnson et al., Abstracts/Neuropharmacology 43 (2002) 291.
Khimia Geterotsiklicheskikh Soedinenii, 1985, vol. 5, PT 1985, 646-649.

Glutamate receptors: brain function and signal transduction, Nakanishi, et al., Brain Research Reviews 26 (1998) 230-235.
Activation of Metabotropic Glutamate Receptor-1 Accelerates NMDA Receptor Trafficking, Lan et al., Abstracts/Neuropharmacology 43 (2002) 294.
Glutamate metabotropic receptors as targets for drug therapy in epilepsy, Moldrich et al., European Journal of Pharmacology 476 (2003) 3-16.
Metabotropic glutamate receptor 2 modulates excitatory synaptic transmission in the rat globus pallidus, Poisik, et al., Neuropharmacology 49 (2005) 57-69.
Pharmacological Characterization and Identification of Amino Acids Involved in the Positive Modulation of Metabotropic Glutamate Receptor Subtype 2, Schaffhauser et al., Mol. Pharmacol 64:798-810, 2003, vol. 64, No. 4.
The metabotropic glutamate receptor 5 antagonist MPEP and the mGluR2 agonist LY379268 modify disease progression in a transgenic mouse model of Huntington's disease, Schiefer, et al., Brain Research 1019 (2004) 246-254.
Phenyl-tetrazolyl Acetophenones: Discovery of Positive Allosteric Potentiators for the Metabotropic Glutamate 2 Receptor, Pinkerton, et al., J. Med. Chem 2004, 47, 4595-4599.
Pharmacological agents acting at subtypes of metabotropic glutamate receptors, Schoepp, Neuropharmacology 38 (1999) 1431-1476.
Group II mGluR receptor agonists are effective in persistent and neuropathic pain models in rats, Simmons, et al., Pharmacology, Biochemistry and Behavior 73 (2002) 419-427.
Preclinical Pharmacology of mGlu2/3 Receptor Agonists: Novel Agents for Schizophrenia?, Schoepp et al., CNS & Neurological Disorders, 2002, 1, 215-225.
Khimia Geterotsiklicheskikh Soedinenii, 1986, vol. 1986, PT 8, 1118-1123.
International Search Report for International Application No. PCT/EP2007/052442 dated Sep. 7, 2007.
Distribution of a metabotropic glutamate receptor, mGluR2, in the central nervous system of the rat and mouse: an immunohistochemical study with a monoclonal antibody, Ohishi, Neuroscience Research 30 (1998) 65-82.
Chemical Abstracts, Azimov et al. abstract No. 78798, vol. 105, No. 10, 1986.
Acta Chimica Slovencia, 2005, vol. 52, No. 4, pp. 391-397.
Al-Orman et al. "Studies with Polyfunctionally Substituted Heteroaromatics: New Routes for the Synthesis of Polyfunctionally Substituted Pyridines and 1,2,4-Triazolo[1,5-a]pyridines", Heteratom. Chemistry, vol. 6, No. 6, 1995, 545-551.
Azimov et al. Chemical Abstracts, 1986, abstract No. 78798, vol. 105 No. 10.
Azume et al., "Synthesis and reactions of 4-choloro-1, 2-dihydro-6-methyl-2-oxo-3-pyridinecarbonitrile", CA139:197340 (2003).
Boatman et al., "Alkylations at the Methyl or alpha-Methylene Group of 6- or 4-Alkyl-3-cyano-2(1)-pyridones through Dianions", Journal of Organic Chemistry, 1965, vol. 30 Pt 11, pp. 3593-3597.
Bohme et al., "Darstellng and Umsetzungen von 3-Arylamino-2-halogencrotononitilen", Chem. Ber., 1976, 109, 2908-2913.
Bradley et al. "Activation of Group II Metabotropic Glutamate Receptors Inhibits Synaptic Excitation of the Subsantia Nigra Pars Reticulata," J. of Neuroscience, May 1, 2000, 20(9):3085-3094.
Braish et al., "Construction of the (1x,5x,6x)-6-Amino-3-azabicyclo[3.1.0]hexane Ring System," Synlett, 1996, 1100-1102.
Brighty et al., "Synthesis of (1x,5x,6x)-6-Amino-3-azabicyclo[3.1.0]hexane, a Novel Achiral Diamine," Synlett, 1996, 1097-1099.
CA Office Action Apr. 23, 2010.
Cartmell et al. "Regulation of Neurotransmitter Release by Metabotropic Glutamate Receptors", J. Neurochem., p. 889-907, vol. 75, No. 3, 2000.
Clark et al., "Synthesis of Thieno[2,3-d]pyrimidines from 4,6-Dichloropyrimidine-5-carbaldehydes", Journal Heterocyclic Chem, 1993, vol. 30, 1065-1072.
Cook et al. "Diethylaminoalkyl Ester Hydrochlorides of N-Alkyl-4-carbostyrilcarboxylic Acids", J Am. Chem. Soc., 1952, 74, 543-554.

DiMichelle et al. "The Natural Course of Schizophrenia and Psychopathological Predictors of Outcome", (Mar.-Apr. 2004), 37(2), pp. 98-104 (abstract).

Duong et al. "A Biogenetic Like Synthesis of Perloline, 6-(3,4-Dimethoxyphenyl)-5-hydroxy-5,6-dihydrobenzo[c][2,7]naphthyridin-4(3H)-one", Aust. J. Chem., 1983, 36, 1431-1440.

Erlenmeyer et al., "Über einige Derivate des 2-Aminothiazols", Helvetica Chim Acta, 1949, 35-38.

Ershov et al., Chemical Abstracts, 1985, vol. 103, Pt 21, pp. 678.

Euraisian Notification on the necessity to present additional matters from the Eurasian Patent Organization dated Dec. 17, 2008.

Feinberg et al, "The selective group mG1u2/3 receptor agonist LY379268 suppresses REM sleep and fast EEG in the rat," Pharmacology, Biochemistry and Behavior 73 (2002) 467-474.

Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.

Galici et al., A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, J of Pharmacology and Experimental Therapeutics, p. 1181-1187, vol. 315, No. 3, (2005).

Ghammamy et al., "Cetyltrimethylammonium Bromochromate: A New and Efficient Oxidant for Organic Substrates", Synthetic Communications, 2007, 37, 599-605.

Govek et al. Benzazoles as allosteric potentiators of metabotropic glutamate receptor 2 (mGluR2): Efficacy in an animal model for schizophrenia, Bioorg. Med. Chem Lett. 15 (2005) 4068-4072.

Grillon, et al., Anxiolytic effects of a novel group II metabotropic glutamate receptor agonist (LY354740) in the fear-potentiated startle paradigm in humans, Psychopharmacology (2003) 168:446-454.

Hamaguchi et al., "Effects of Hetero Atom Substituents in the decomposition of Pyrazolines: Abnormal Behavior of Methoxy Group Compared with Arylthio of Arylseleno Group.", Heterocycles, 1986, vol. 24, 2111-2115.

Hanfeld et al. "Synthese von 3-Cyan-6-methyl-4-pyridyl-und 3-cyan-4-methyl-6-pyridyl-pyrid-2(1H)-onen und -thionen", Pharmazie 43 (1988), H.11, 762-764.

Haper, "Agonist-Stimulated [35S]GTPyS Binding," Current Protocols in Pharmacology, 1998, Unit 2.6, 1-10.

Harriman et al. "Synthesis of 4-Substituted 4-Arylpiperidines", Tetrahedron Letters, 2000, 41, 8853-8856.

Helton et al. "Anxiolytic and Side-Effect Profile fo LY354740: A Potent, Highly Selective, Orally Active Agonist for Group II Metobotropic Glutamate Receptors", Journal of Phamacology and Experimental Therapeutics, 1998, 284, 2, 651-660.

Holden, "Excited by Glutamate", Science, p. 1866-1868, vol. 300, Jun. 20, 2003.

Hughes, "Progress in the Mitsunobu Reaction. A Review," Organic Preparations and Procedures International, 1996, 127-164.

Hughes, "The Mitsunobu Reaction", Organinc Reactions, 1992, vol. 42, 335-656.

International Search Report dated Oct. 26, 2009 for international application No. PCT/EP2009/006326.

Jain et al. "A One-Step Preparation of Functionalized 3-Cyano-2-Pyridones", Tetrahedron Letters, 1995, 36, 19, 3307-3310.

Johnson et al. Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylmethyl-amine', J. Med. Chem. 2003, 46, 3189-3192.

Johnson et al. Allosteric modulators of metabotropic glutamate receptors: lessons learnt from mGlu1, mGlu2 and mGlu5 potentiators and antagonists, Biochemical Society Transactions (2004) vol. 32, part 5, 881-887.

Johnson et al., Selective, Non-Amino Acid Allosteric mGlu2 Receptor Potentiators Inhibit Dural Plasma Protein Extravasation; A Potential Role In the Treatment of Migraine, Abstracts/Neuropharmacology 43 (2002) 291.

Kambe et al "A Convenient Method for the Preparation of 2-Pyridone Derivatives", 1977, vol. 12, pp. 841-842.

Kellner et al., Effects of metabotropic glutamate2/3 receptor agonist (LY544344/LY354740) on panic anxiety induced by cholecystokinin tetrapeptide in health humans: preliminary results, Psychopharmacology (2005) 179: 310-315.

Kilama et al. "A New Synthstic Approach to the C-D Ring Portion of Streptonigrin Analogues" Journal of Heterocyclic Chemistry, 1990, 27, 1437-1440.

Kiselyov et al., "A one pot synthesis of polysubstituted inidazo[1,2-a]pyridines", Tetrahedron Letters, 2006, 47, 2941-2944.

Kitano et al., "Synthesis and antifouling activity of 3-isocyanotheonellin and its analogues", Jour Chem Soc Perkin Trans, 2002, 2251-2255, The Royal Society of Chemistry.

Klemm et al. "Chemistry of Thienopyridines. VIII. Substitution Products Derived from Thieno[2,3-b] pyridine 7-Oxide (1)", Journal of Heterocyclic Chemistry, 1970, 7(1), 81-89.

Lan et al., Activation of Metabotropic Glutamate Receptor-1 Accelerates NMDA Receptor Trafficking, Abstracts/Neuropharmacology 43 (2002) 294.

Larock, "Comprehensive Organic Transformations", VCH Publishers, 1989, 595-596.

Lee et al., "Benzylic Bromination of Alkylbenzenes with Sodium Bromate-Bromotrimethylsilane", Bull. Korean Chem. Soc, 1995, vol. 16, pp. 371-374.

Malames et al. "N-Substituted Spirosuccinimide, Spiropyridazine, Spiroazetidine, and Acetic Acid Aidose Reductase Inhibitiors Derived From Isoquinoline-1,3-dinoes. 2", J Med Chem., 1994, 37(13), 2059-2070.

McElvain et al. "Piperidine Derivatives. XXX. 1,4-Dialkyl-4-arylpiperidines", J. Am. Chem. Soc, 1958, 80, 3915-3923.

Moldrich et al., Glutamate metabotropic receptors as targets for drug therapy in epilepsy, European Journal of Pharmacology 476 (2003) 3-16.

Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.

Moore et al. "Cycloadditions of Cyanoketenes to Cinnamylideneamines and Benzylideneamines. Synthetic Scope, Stereochemistry, and Mechanism", Journal Org. Chem. 1985, 50, 4231-4238.

Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508.

Mutel et al., "Characterization of (2S,2'R,3'R)-2-(2',3'-[3H]-Dicarboxycyclopropyl)glycine Binding in Rat Brain," J Neurochemistry, 71(6), 1998, 2558-2564.

Mutel, "Therapeutic potential of non-competitive, subtype-selective metabotropic glutamate receptor ligands", Expert Opin. Ther. Patents (2002), 12 (12) p. 1845-1852.

Nakamura et al., "An Efficient Synthesis of Platelet-Activating Factor (PAF) J'IJ I-QALKYL-2----(3-ISOXAZOLYL)-SN__GLYCERO-3-PHOSPHOCHOLINE, a New PAF Agonist. Utilization of the 3-ISOXAZOLYLOXY Group as a Protected Hydroxyl." Tetrahedron Letters, 1990, vol. 31, 699-702.

Nakanishi, et al., Glutamate receptors: brain function and signal transduction, Brain Research Reviews 26 (1998) 230-235.

Nakano et al. "1-Alkyl-3-phenylpyridinium 1-Alkyl-2(1H)-pyridone 3-Phenyl 5-Phenyl", Annual Report of Tohoku College of Pharmacy, 1998, 45, 145-148.

Nell et al., "Preparation of 4-amino-3,5-dicyano-2-thiopyridines as cardiovascular agents", CA149:32326 (2008).

Ohishi et al., "Distribution of a metabotropic glutamate receptor, mGluR2, in the central nervous system of the rat and mouse: an immunohistochemical study with a monoclonal antibody," Neuroscience Research 30 (1998) 65-82.

Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.

Pin et al., "New perspectives for the development of selective metabotropic glutamate receptor ligands," European J of Pharmacology, 1999, 375, 277-294.

Pinkerton, et al., Phenyl-tetrazolyl Acetophenones: Discovery of Positive Allosteric Potentiators for the Metabotropic Glutamate 2 Receptor, J. Med. Chem 2004, 47, 4595-4599.

Poisik, et al., Metabotropic glutamate receptor 2 modulates excitatory synaptic transmission in the rat globus pallidus, Neuropharmacology 49 (2005) 57-69.

Potts et al. "1,2,4-Triazoles. XII. Derivatives of the s-Triazolo[4,3-a]pyridine Ring System", Journal of Organic Chemistry, 1966, 251-260.

Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.

Prager et al. "The Synthesis of Peroline, 6-(3,4-Dimethoxyphenyl)-5-hydroxy-5,6-dihydrobenzo[c][2,7]naphthyridin-4 (3H)-one", Aust. J. Chem., 1983, 36, 1441-1453.

Rani et al. "Thiazoline Analogues of Epiderstatin, New Inhibitiors of Cell Cycle of TsFT-210 Cells", Journal of Antibiotics, 1995, 48(10), 1179-1181.

Renslo et al., "Synthesis of Aza-, Oxa-, and Thiabicyclo[3.1.0]hexane Heterocycles from a Common Synthetic Intermediate," Organic Letters, 2005, vol. 7, No. 13, 2627-2630, American Chemical Society, USA.

Roma et al., "1,8-Naphthyridines VII. New substituted 5-amino[I,2,4]triazolo[4,3-a] [1 ,8]naphthyridine-6-carboxamides and their isosteric analogues, exhibiting notable anti-inflammatory and/or analgesic activities, but no acute gastrolesivity", European Journal of Medical Chemistry. 2008, 43, 1665-1680.

Rosowsky et al. "2,4-Diaminothieno[2,3-d]pyrimidines as Antifolates and Antimalarials. 3. synthesis of 5,6-Disubstituted Derivatives and Related Tetracyclic Analogs", Journal of Medicinal Chemistry, 1973, 16,3,191-194.

Ryndina, et al., Torp-Ziegler Cyclization in the Synthesis of 3-Amino-4-Cyanopyrrole Derivatives, Chemistry of Heterocyclic Compounds, vol. 36, No. 12, 2000, pp. 1409-1420.

Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998/.

Schaffhauser et al., "Pharmacological Characterization and Identification of Amino Acids Involved in the Positive Modulation of Metabotropic Glutamate Receptor Subtype 2," Mol. Pharmacol 64:798-810, 2003, vol. 64, No. 4.

Schiefer et al. "The metabotropic glutamate receptor 5 antagonist MPEP and the mGluR2 agonist LY379268 modify disease progression in a transgenic mouse model of Huntington's disease," Brain Research 1019 (2004) 246-254.

Schoepp et al, "Pharmacological agents acting at subtypes of metabotropic glutamate receptors," Neuropharmacology 38 (1999) 1431-1476.

Schoepp et al., "Preclinical Pharmacology of mGlu2/3 Receptor Agonists: Novel Agents for Schizophrenia?", CNS & Neurological Disorders, 2002, 1, 215-225.

Senda et al. "Ring Transformation of Uracils to 2-Pyridones. Hydrolysis of 6-(Dimethylaminovinyl) Uracils" Heterocycles, 1978, 9, 6, 1-6.

Shiba et al. "Synthesis and binding affinities of methylvesamicol analogs for the acetylcholine transporter and sigma receptor", Bioorganic and Medicinal Chemistry, 2006, 14, 2620-2626.

Simmons et al., "Group II mGluR receptor agonists are effective in persistent and neuropathic pain models in rats," Pharmacology, Biochemistry and Behavior 73 (2002) 419-427.

SIPO Office Action Jun. 30, 2010.

Stewart et al. "Discovery of Inhibitors of Cell Adhesion Molecule Expression in Human Endothelial Cell. 1. Selective Inhibition of ICAM-1 and E-Selectin Expression", J Med Chem, 2001, 44, 998-1002.

Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505.

Tutonda et al. "Diels-Alder Reactions of the Heterodiene System in 2(1H)-Pyrazinones", Tetrahedron Letters, 1986, 27, 22, 2509-2512.

VanAllan et al. "Reactions of Some 4-Methylene-4H-pyran Derivatives with Primary and Secondary Amines", Journal of Heterocyclic Chemistry, 1970, 7, 495-507.

Vilsmaier et al., "Diastereoselective Syntheses of N-Protected Derivatives of 1a,5a,6fi-6-Amino-3-azabicyclo [3.101] hexane; A Route to Trovafloxacin 6fl-Diastereomer," Synthesis, 1998, 739-744.

Vippagunta et al., Crystalline Solids, Adv. Drug Deily. Rev., 2001, 48, pp. 3-26.

Wang et al. "A simple and efficient automatable one step synthesis of triazolopyridines form carboxylic acids", Tetrahedron Letters, 2007, 48, 2237-2240.

Watanbe et al. "Pd/P(t-Bu)3-Catalyzed Synthesis of Aromatic Amines", Journal of TOSOH Research, 1999, vol. 43, 38-50.

Wenner et al, "Derivatives of 2-Pyridone", Journal of Organic Chemistry, 1946, vol. 11, pp. 751-759.

West Anthony R. Solid State Chemistry and Its Applications, Wiley, New York, 1988 pp. 358 & 365.

Yalyaheva et al., Chemical Abstract, Heterocycles, p. 687, vol. 107, 1987.

* cited by examiner

1,4-DISUBSTITUTED 3-CYANO-PYRIDONE DERIVATIVES AND THEIR USE AS POSITIVE MGLUR2-RECEPTOR MODULATORS

IN THE CROSS-REFERENCE TO RELATED APPLICATIONS

This application claims priority to (EP) Application No. 07103654.5, filed Mar. 7, 2007; PCT International Application No. PCT/EP2007/052442, filed Mar. 15, 2007; and (EP) Application No. 07116402.4, filed Sept. 14, 2007, which are hereby incorporated herein by reference in their entirety for all purposes.

FIELD OF THE INVENTION

The present invention relates to novel pyridin-2-one-derivatives which are positive allosteric modulators of the metabotropic glutamate receptor subtype 2 ("mGluR2") and which are useful for the treatment or prevention of neurological and psychiatric disorders associated with glutamate dysfunction and diseases in which the mGluR2 subtype of metabotropic receptors is involved. The invention is also directed to pharmaceutical compositions comprising such compounds, to processes to prepare such compounds and such compositions, and to the use of such compounds for the prevention or treatment of neurological and psychiatric disorders and diseases in which mGluR2 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission.

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signaling pathways.

The mGluR2 subtype is negatively coupled to adenylate cyclase via activation of Gαi-protein, and its activation leads to inhibition of glutamate release in the synapse. In the central nervous system (CNS), mGluR2 receptors are abundant mainly throughout cortex, thalamic regions, accessory olfactory bulb, hippocampus, amygdala, caudate-putamen and nucleus accumbens.

Activating mGluR2 was shown in clinical trials to be efficacious to treat anxiety disorders. In addition, activating mGluR2 in various animal models was shown to be efficacious, thus representing a potential novel therapeutic approach for the treatment of schizophrenia, epilepsy, addiction/drug dependence, Parkinson's disease, pain, sleep disorders and Huntington's disease.

To date, most of the available pharmacological tools targeting mGluRs are orthosteric ligands which activate several members of the family as they are structural analogs of glutamate.

A new avenue for developing selective compounds acting at mGluRs is to identify compounds that act through allosteric mechanisms, modulating the receptor by binding to a site different from the highly conserved orthosteric binding site.

Positive allosteric modulators of mGluRs have emerged recently as novel pharmacological entities offering this attractive alternative. Various compounds have been described as mGluR2 positive allosteric modulators.

WO2004/092135 (NPS & Astra Zeneca), WO2004/018386, WO2006/014918 and WO2006/015158 (Merck), WO2001/56990 (Eli Lilly) and WO2006/030032 (Addex & Janssen Pharmaceutica) describe respectively phenyl sulfonamide, acetophenone, indanone, pyridylmethyl sulfonamide and pyridinone derivatives as mGluR2 positive allosteric modulators. None of the specifically disclosed compounds are structurally related to the compounds of the invention.

WO2007/104783 describes 1,4-disubstituted 3-cyano-pyridone-derivatives that are positive allosteric modulators of metabotropic receptors-subtype 2 ("mGluR2").

It was demonstrated that such compounds do not activate the receptor by themselves. Rather, they enable the receptor to produce a maximal response to a concentration of glutamate which by itself induces a minimal response. Mutational analysis has demonstrated unequivocally that the binding of mGluR2 positive allosteric modulators does not occur at the orthosteric site, but instead at an allosteric site situated within the seven transmembrane region of the receptor.

Animal data are suggesting that positive allosteric modulators of mGluR2 have effects in anxiety and psychosis models similar to those obtained with orthosteric agonists. Allosteric modulators of mGluR2 were shown to be active in fear-potentiated startle, and in stress-induced hyperthermia models of anxiety. Furthermore, such compounds were shown to be active in reversal of ketamine- or amphetamine-induced hyperlocomotion, and in reversal of amphetamine-induced disruption of prepulse inhibition of the acoustic startle effect models of schizophrenia (J. Pharmacol. Exp. Ther. 2006, 318, 173-185; Psychopharmacology 2005, 179, 271-283).

Recent animal studies further reveal that the selective positive allostric modulator of metabotropic glutamate receptor subtype 2 biphenyl-indanone (BINA) blocks a hallucinogenic drug model of psychosis, supporting the strategy of targeting mGluR2 receptors for treating glutamatergic dysfunction in schizophrenia (Mol. Pharmacol. 2007, 72, 477-484).

Positive allosteric modulators enable potentiation of the glutamate response, but they have also been shown to potentiate the response to orthosteric mGluR2 agonists such as LY379268 or DCG-IV. These data provide evidence for yet another novel therapeutic approach to treat above mentioned neurological and psychiatric diseases involving mGluR2, which would use a combination of a positive allosteric modulator of mGluR2 together with an orthosteric agonist of mGluR2.

The present compounds are characterized by a central pyridine-2-one moiety substituted in position 3 with cyano and in position 4 with optionally substituted phenyl which is on its turn substituted in position 4 with substituted pyridinyloxy.

The present compounds are potent positive allosteric mGluR2 modulators and exhibit improved cardiovascular safety profile.

DESCRIPTION OF THE INVENTION

The invention relates to compounds having metabotropic glutamate receptor 2 modulator activity. The present invention provides a compound according to formula (I),

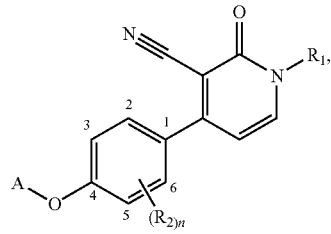

(I)

including any stereochemically isomeric form thereof, wherein
$R_1$ is $C_{4-6}$alkyl, or $C_{1-3}$alkyl substituted with $C_{3-7}$cycloalkyl;
$R_2$ is hydrogen or halo;
A is pyridinyl substituted with one or two substituents, each substituent independently selected from halo or $C_{1-4}$alkyl;
n is an integer of value 1 or 2;
or a pharmaceutically acceptable salt or a solvate thereof;
provided that if $R_2$ is 2-fluoro then A is not 3-pyridinyl substituted with one or two substituents, each substituent independently selected from halo or $C_{1-4}$alkyl.

The present invention also relates to the use of a compound of formula (I) or any subgroup thereof for the manufacture of a medicament for treating or preventing, in particular for treating, a condition in a mammal, including a human, the treatment or prevention of which is affected or facilitated by the neuromodulatory effect of an allosteric modulator of mGluR2, in particular a positive allosteric modulator.

An embodiment of the present invention are those compounds of formula (I)

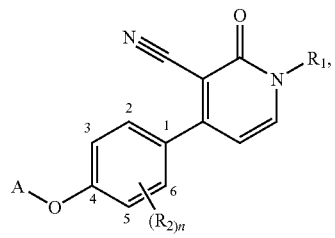

(I)

including any stereochemically isomeric form thereof, wherein
$R_1$ is $C_{4-6}$alkyl, or $C_{1-3}$alkyl substituted with $C_{3-7}$cycloalkyl;
$R_2$ is hydrogen or halo;
A is pyridinyl substituted with one or two substituents, each substituent independently selected from halo or $C_{1-4}$alkyl;
n is an integer of value 1 or 2;
or a pharmaceutically acceptable salt or a solvate thereof;
provided that if $R_2$ is 2-fluoro then A is not 3-pyridinyl substituted with one or two substituents, each substituent independently selected from halo or $C_{1-4}$alkyl; and
provided that the compound is other than

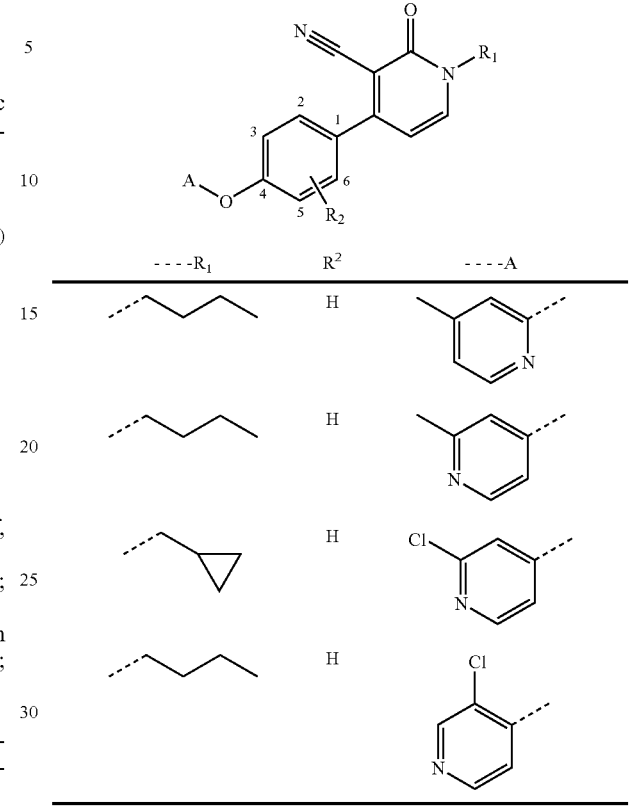

An embodiment of the present invention are those compounds of formula (I) wherein $R_1$ is $C_{4-6}$alkyl, in particular $C_{4-5}$alkyl, such as for example 1-butyl, 2-methyl-1-propyl, 3-methyl-1-butyl; in particular 1-butyl or 3-methyl-1-butyl; more in particular 1-butyl.

An embodiment of the present invention are those compounds of formula (I) wherein $R_1$ is $C_{1-3}$alkyl substituted with $C_{3-7}$cycloalkyl, in particular cyclopropylmethyl or 2-(cyclopropyl)-1-ethyl, more in particular cyclopropylmethyl.

An embodiment of the present invention are those compounds of formula (I) or any subgroup thereof as mentioned hereinbefore as embodiment, wherein $R_2$ is hydrogen or fluoro, in particular fluoro.

An embodiment of the present invention are those compounds of formula (I) or any subgroup thereof as mentioned hereinbefore as embodiment, wherein $R_2$ is halo, in particular fluoro.

An embodiment of the present invention are those compounds of formula (I) or, whenever possible, any subgroup thereof as mentioned hereinbefore as embodiment, wherein n is 1 and $R_2$ is hydrogen.

An embodiment of the present invention are those compounds of formula (I) or, whenever possible, any subgroup thereof as mentioned hereinbefore as embodiment, wherein n is 1 and $R_2$ is halo, in particular fluoro.

An embodiment of the present invention are those compounds of formula (I) or, whenever possible, any subgroup thereof as mentioned hereinbefore as embodiment, wherein n is 2 and $R_2$ is halo, in particular fluoro.

An embodiment of the present invention are those compounds of formula (I) or, whenever possible, any subgroup thereof as mentioned hereinbefore as embodiment, wherein n is 1 and R₂ is halo, in particular fluoro, and placed in ortho position compared to the pyridinone moiety, i.e. in position 2.

An embodiment of the present invention are those compounds of formula (I) or, whenever possible, any subgroup thereof as mentioned hereinbefore as embodiment, wherein n is 1 and R₂ is halo, in particular fluoro, and placed in meta position compared to the pyridinone moiety, i.e. in position 3.

An embodiment of the present invention are those compounds of formula (I) or, whenever possible, any subgroup thereof as mentioned hereinbefore as embodiment, wherein n is 2 and R₂ is halo, in particular fluoro, and the R₂ substituents are placed in meta position compared to the pyridinone moiety, i.e. in positions 3 and 5.

An embodiment of the present invention are those compounds of formula (I) or, whenever possible, any subgroup thereof as mentioned hereinbefore as embodiment, wherein n is 2 and R₂ is halo, in particular fluoro, and the R₂ substituents are placed in ortho position compared to the pyridinone moiety, i.e. in positions 2 and 6.

An embodiment of the present invention are those compounds of formula (I) or, whenever possible, any subgroup thereof as mentioned hereinbefore as embodiment, wherein A is substituted 2-pyridinyl.

An embodiment of the present invention are those compounds of formula (I) or, whenever possible, any subgroup thereof as mentioned hereinbefore as embodiment, wherein A is substituted 3-pyridinyl.

An embodiment of the present invention are those compounds of formula (I) or, whenever possible, any subgroup thereof as mentioned hereinbefore as embodiment, wherein A is substituted 4-pyridinyl.

An embodiment of the present invention are those compounds of formula (I) or, whenever possible, any subgroup thereof as mentioned hereinbefore as embodiment, wherein the pyridinyl ring represented by A is substituted with one substituent selected from halo, in particular fluoro, or C₁₋₄alkyl, in particular methyl.

An embodiment of the present invention are those compounds of formula (I) or, whenever possible, any subgroup thereof as mentioned hereinbefore as embodiment, wherein the pyridinyl ring represented by A is substituted with two substituents, each substituent independently being selected from halo, in particular chloro, or C₁₋₄alkyl, in particular methyl.

An embodiment of the present invention are those compounds of formula (I), wherein R₁ is C₄₋₆alkyl, in particular 1-butyl or 3-methyl-1-butyl; or C₁₋₃alkyl substituted with C₃₋₇cycloalkyl, in particular cyclopropylmethyl or 2-(cyclopropyl)-1-ethyl;
R₂ is hydrogen or fluoro;
n is 1 or 2;
A is pyridinyl substituted with one or two substituents, each substituent independently being selected from methyl or chloro.

An embodiment of the present invention are those compounds of formula (I) selected from,

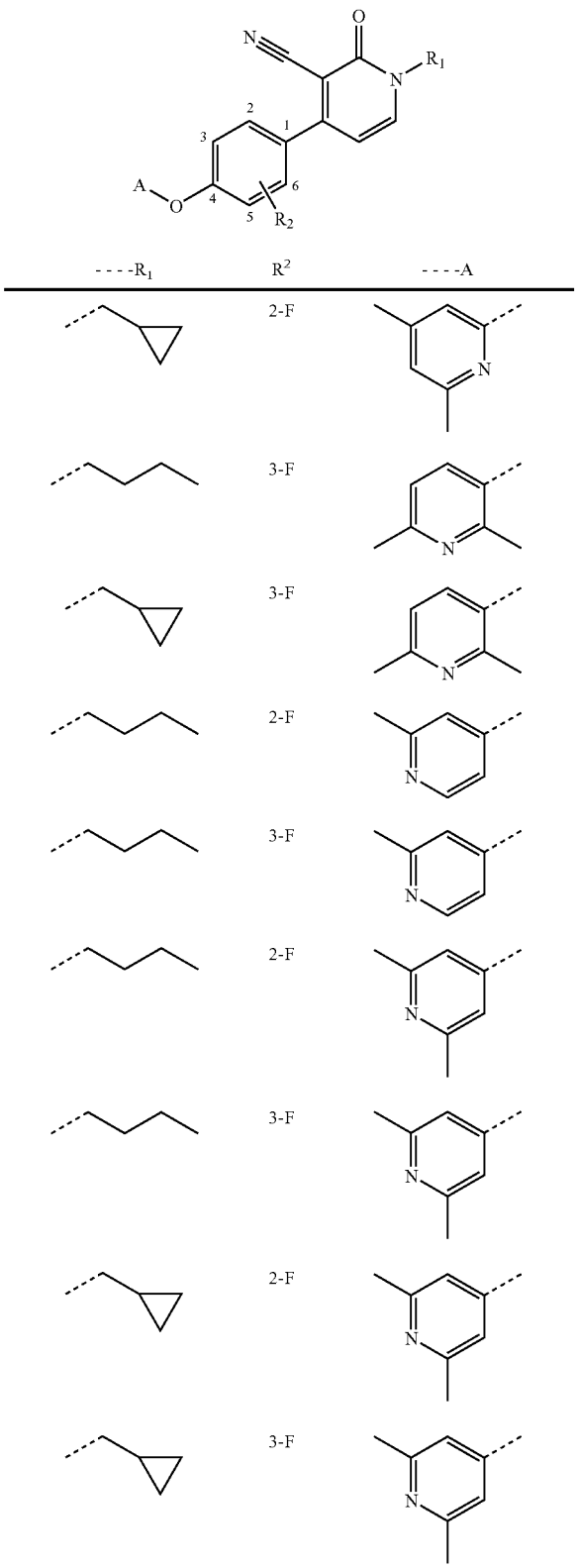

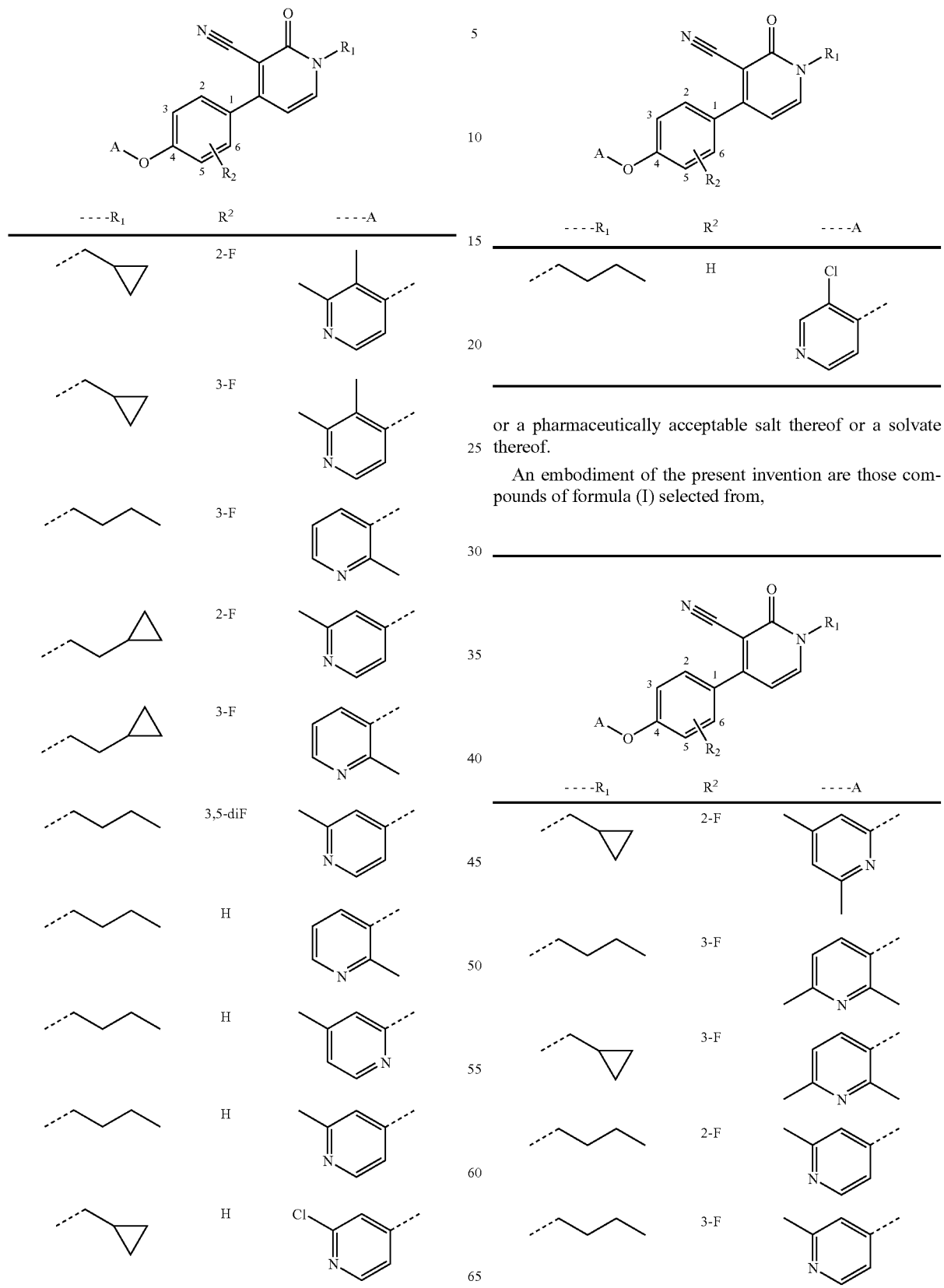
or a pharmaceutically acceptable salt thereof or a solvate thereof.
An embodiment of the present invention are those compounds of formula (I) selected from,

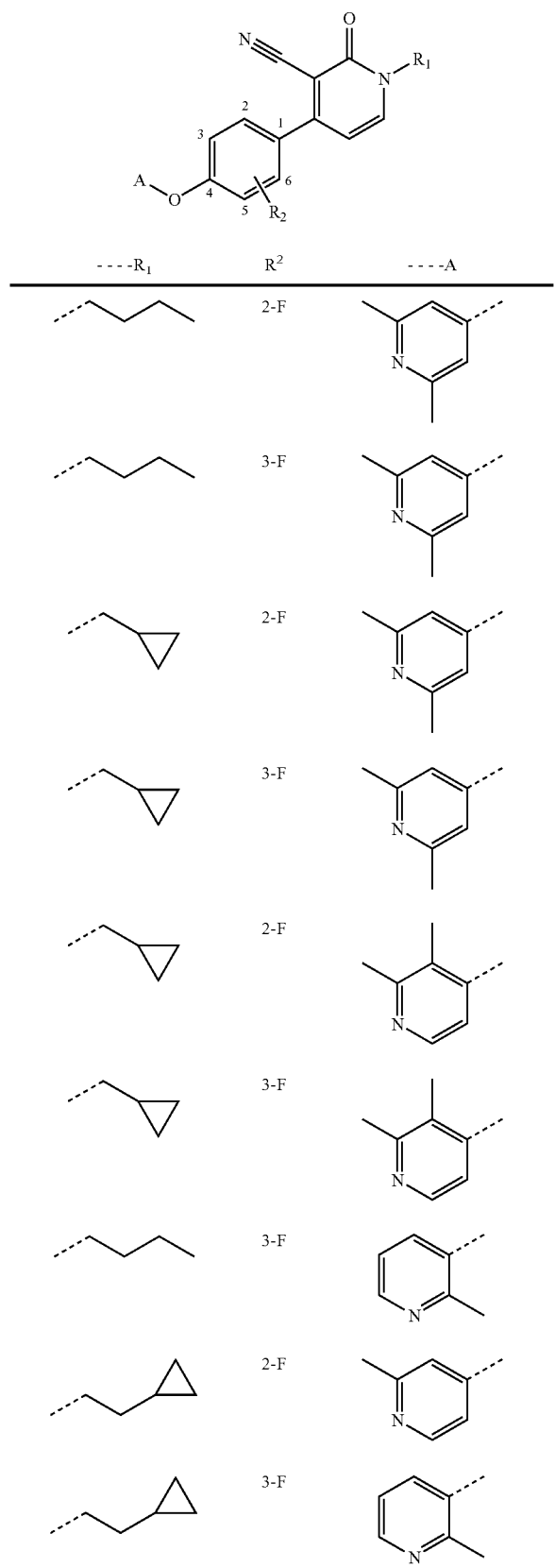

or a pharmaceutically acceptable salt thereof or a solvate thereof.

As used hereinbefore or hereinafter, the notation $C_{1-3}$alkyl as a group or part of a group defines a saturated, straight or branched, hydrocarbon radical having from 1 to 3 carbon atoms, such as methyl, ethyl, 1-propyl and 1-methyl-1-ethyl. Preferably $C_{1-3}$ alkyl represents methyl.

As used hereinbefore or hereinafter, the notation $C_{1-4}$alkyl as a group or part of a group defines a saturated, straight or branched, hydrocarbon radical having from 1 to 4 carbon atoms such as methyl, ethyl, propyl, 1-methyl-1-ethyl, 1-butyl, 2-methyl-1-propyl. Preferably, $C_{1-4}$alkyl represents methyl.

As used hereinbefore or hereinafter, the notation $C_{4-6}$alkyl as a group or part of a group defines a saturated, straight or branched, hydrocarbon radical having from 4 to 6 carbon atoms such as 1-butyl, 2-methyl-1-propyl, 1-pentyl, 2-methyl-1-butyl, 3-methyl-1-butyl, 1-hexyl and the like. Preferably $C_{4-6}$alkyl represents 1-butyl.

As used hereinbefore or hereinafter, the notation $C_{4-5}$alkyl as a group or part of a group defines a saturated, straight or branched, hydrocarbon radical having 4 or 5 carbon atoms such as 1-butyl, 2-methyl-1-propyl, 1-pentyl, 2-methyl-1-butyl, 3-methyl-1-butyl and the like.

As used hereinbefore or hereinafter, the notation $C_{3-7}$cycloalkyl defines a saturated, cyclic hydrocarbon radical having from 3 to 7 carbon atoms, such as cyclopropyl, cyclobutyl, cyclopentyl, cyclohexyl and cycloheptyl. Preferably $C_{3-7}$cycloalkyl represents cyclopropyl.

As used hereinbefore or hereinafter, the notation halo is generic to fluoro, chloro, bromo and iodo.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to formula (I) are able to form. Said salts can be obtained by treating the base form of the compounds according to formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid salt forms can be converted into the free base form by treatment with an appropriate base.

The compounds according to formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said base salt forms can be converted into the free acid forms by treatment with an appropriate acid.

The pharmaceutically acceptable acid addition salt forms of the compounds of formula (I) are the preferred pharmaceutically acceptable salt forms of the compounds of formula (I).

The term solvate comprises the solvent addition forms as well as the pharmaceutically acceptable salts thereof, which the compounds of formula (I) are able to form. Examples of such solvent addition forms are e.g. hydrates, alcoholates and the like.

It will be appreciated that some of the compounds of formula (I) and their salts and solvates may contain one or more centers of chirality and exist as stereochemically isomeric forms.

The term "stereochemically isomeric forms" as used hereinbefore defines all the possible isomeric forms that the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. But the invention also embraces each of the individual isomeric forms of formula (I) and their salts or solvates, substantially free, i.e. associated with less than 10%, preferably less than 5%, in particular less than 2% and most preferably less than 1% of the other isomers. Thus, when a compound of formula (I) is for instance specified as (R), this means that the compound is substantially free of the (S) isomer.

In particular, stereogenic centers may have the R- or S-configuration; substituents on bivalent cyclic (partially) saturated radicals may have either the cis- or trans-configuration.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Whenever used hereinafter, the term "compounds of formula (I)" or any subgroup thereof, is meant to also include their stereochemically isomeric forms, their pharmaceutically acceptable salts and their solvates. Of special interest are those compounds of formula (I) which are stereochemically pure.

In the framework of this application, an element, in particular when mentioned in relation to a compound according to formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluor is mentioned, it is understood to refer to $^{18}F$, $^{19}F$ or mixtures thereof. The compounds according to the invention therefore also comprise compounds with one or more isotopes of one or more element, and mixtures thereof, including radioactive compounds, also called radio labelled compounds, wherein one or more non-radioactive atoms has been replaced by one of its radioactive isotopes. In particular, the radioactive atom is selected from the group of hydrogen, carbon, nitrogen, sulfur, oxygen and halogen. Preferably, the radioactive atom is selected from the group of hydrogen, carbon and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Whenever used hereinbefore or hereinafter that substituents can be selected each independently out of a list of definitions, all possible combinations are intended which are chemically possible.

Lines drawn from substituents into ring systems indicate that the bond may be attached to any of the suitable ring atoms.

In general, compounds of formula (I) can be prepared according to the below Experimental procedures 1.

Experimental Procedure 1

Compounds of formula (I) can be prepared by reacting an intermediate of formula (II) wherein Y represents a group suitable for Pd mediated coupling with boronic acids or boronic esters, such as, for example, a halo or triflate, with an intermediate of formula (III) wherein $R_3$ and $R_4$ represent hydrogen or $C_{1-4}$alkyl, or wherein $R_3$ and $R_4$ may be taken together to form for example the bivalent radical of formula —$CH_2CH_2$—, —$CH_2CH_2CH_2$—, or —$C(CH_3)_2C(CH_3)_2$—, according to Reaction Scheme (1). The reaction may be performed in a suitable reaction-inert solvent, such as, for example, 1,4-dioxane or mixtures of inert solvents such as, for example, 1,4-dioxane/DMF, in the presence of a suitable base, such as, for example, aqueous $NaHCO_3$ or $Na_2CO_3$, a suitable catalyst, such as for example a Pd-complex catalyst such as, for example, $Pd(PPh_3)_4$, under thermal conditions such as, for example, heating the reaction mixture at 150° C. under microwave irradiation, during for example 10 minutes.

In Reaction Scheme (1), all variables are defined as in formula (I) or as defined hereinabove.

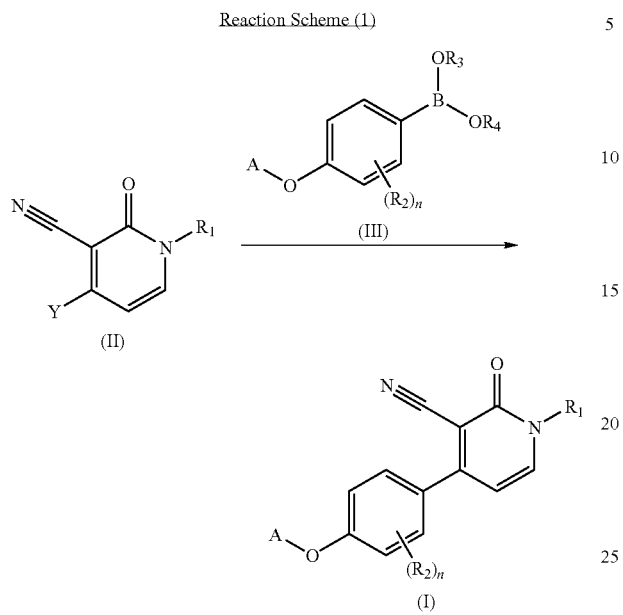

The compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, chiral liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereo specifically.

An alternative manner of separating the enantiomeric forms of the compounds of formula (I) and intermediates involves liquid chromatography or SCF (Super Critical Fluid) chromatography, in particular using a chiral stationary phase.

Some of the intermediates and starting materials are known compounds and may be commercially available or may be prepared according to art-known procedures.

The intermediates can also be prepared according to the below Experimental procedures 2 to 10.

Experimental Procedure 2

Intermediates of formula (II) wherein Y represents halo, said intermediates being represented by formula (II-a), can be prepared by reacting an intermediate of formula (IV) with a suitable halogenating agent such as, for example, $P(=O)Br_3$ according to Reaction Scheme (2). The reaction may be performed in a suitable reaction-inert solvent such as, for example, DMF, at a moderately elevated temperature such as, for example, 110° C. In reaction scheme (2), all variables are defined as in formula (I).

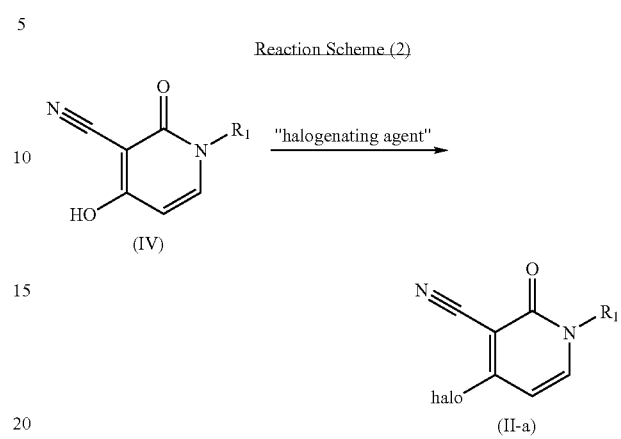

Experimental Procedure 3

Intermediates of formula (II) wherein Y represents $F_3C-S(=O)_2-O-$, said intermediates being represented by formula (II-b), can be prepared by reacting an intermediate of formula (IV) with triflic anhydride (also called trifloromethanesulfonic anhydride) according to Reaction Scheme (3). The reaction may be performed in a suitable reaction-inert solvent such as, for example, dichloromethane, in the presence of a suitable base such as, for example, pyridine at a low temperature such as, for example, −78° C. In Reaction Scheme (3), all variables are defined as in formula (I).

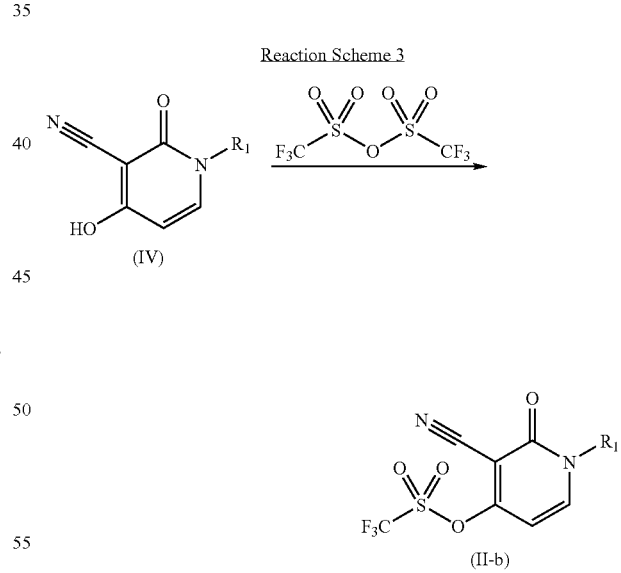

Experimental Procedure 4

Intermediates of formula (IV) can be prepared by art-known procedures by reacting an intermediate of formula (V) with a suitable reagent for methylether-cleavage, such as, for example, NaOH, according to Reaction Scheme (4). The reaction can be performed in a suitable solvent such as, for example, water, THF, at a moderately high temperature such as, for example, 100° C. In Reaction Scheme (4), all variables are defined as in formula (I).

Reaction Scheme (4)

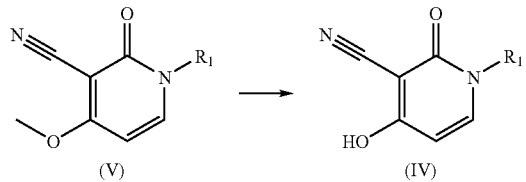

Experimental Procedure 5

Intermediates of formula (V) can be prepared by art-known procedures by reacting commercially available 4-methoxy-2-oxo-1,2-dihydro-pyridine-3-carbonitrile with an alkylating agent of formula (VI), wherein Z represents a suitable leaving group, such as for example halo, e.g. bromo and the like, according to Reaction Scheme (5). An example of an alkylating agent of formula (VI) is for example cyclopropylmethylbromide. The reaction can be performed in an inert solvent such as, for example, acetonitrile, using a suitable base such as, for example, $K_2CO_3$, and, optionally an iodine salt such as for example KI, at a moderately high temperature such as, for example, 120° C. In reaction scheme (5), all variables are defined as in formula (I).

Reaction Scheme (5)

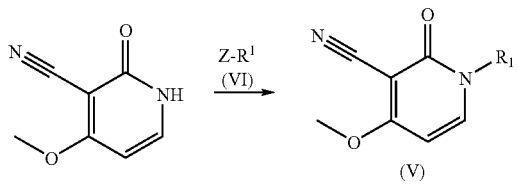

Experimental Procedure 6

Intermediates of formula (III) can be prepared by art-known procedures by reacting an intermediate of formula (VII) wherein A' represents a pyridinyl moiety A as defined hereinabove for formula (I) or a N-oxide thereof, with a suitable boron source such as, for example, bis(pinacolato)diborane in the presence of a suitable palladium catalyst such as, for example, 1,1'-bis(diphenylphosphino)ferrocenepalladium(II) dichloride according to Reaction Scheme (6). The reaction may be performed in an inert solvent such as, for example, dichloromethane, in the presence of a suitable salt such as, for example, potassium acetate, at moderately elevated temperature such as, for example, 110° C. during for example 16 hours.

Alternatively, intermediates of formula (III) can also be prepared by art-known procedures of metal-halogen exchange and subsequent reaction with an appropriate boron source from intermediates of formula (VII). For example, an intermediate of formula (VII) can be reacted with an organolithium compound such as, for example, n-butyllithium, at a moderately low temperature such as, for example, −40° C., in an inert solvent such as, for example, THF, followed by subsequent reaction with an appropriate boron source such as, for example, trimethoxyborane.

In reaction scheme (6), all variables are defined as in formula (I) or as defined hereinabove.

Reaction Scheme (6)

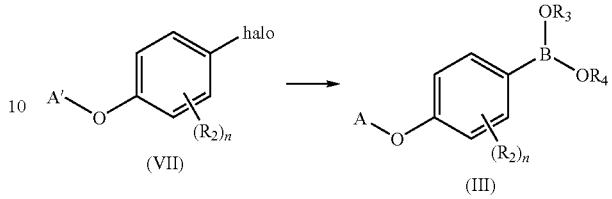

Experimental Procedure 7

Intermediates of formula (VII) can be prepared by art-known procedures by reacting a hydroxyphenol intermediate of formula (VIII) with a suitable intermediate of formula (IX) wherein X is a suitable leaving group such as, for example, halo or nitro, according to Reaction Scheme (7). Examples of intermediates of formula (IX) are 2,3-dimethyl-4-nitro-pyridine 1-oxide and 2-bromo-4,6-dimethylpyridine. The reaction may be performed in an inert solvent such as, for example, dimethylformamide or xylene, in the presence of a suitable base such as, for example, sodium hydride or potassium carbonate, at moderately elevated temperature such as, for example, 180° C. during for example 60 minutes either under classical or microwave irradiation heating. In reaction scheme (7), all variables are defined as in formula (I).

Reaction Scheme (7)

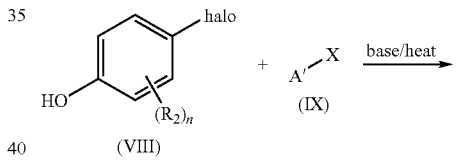

Experimental Procedure 8

Intermediates of formula (VII) wherein A' represents A, said intermediates being represented by formula (VII-a), can be prepared by art-known procedures from an aniline-like intermediate of formula (X) via a Sandmeyer type reaction according to reaction Scheme (8).

In reaction scheme (8), all variables are defined as in formula (I).

Reaction Scheme (8)

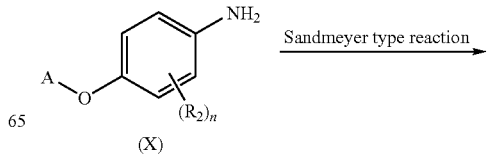

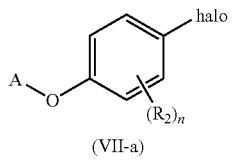

(VII-a)

Experimental Procedure 9

Intermediates of formula (X) can be prepared by art-known procedures from the corresponding nitro intermediate of formula (XI) via reduction of the nitro group to the amino function by art-know procedures such as catalytic hydrogenation by using a suitable catalyst, such as for example palladium 10% on activated carbon or the use of tin(II) chloride dihydrate as a reducting agent, according to Reaction Scheme (9). In Reaction Scheme (9), all variables are defined as in formula (I).

Reaction Scheme (9)

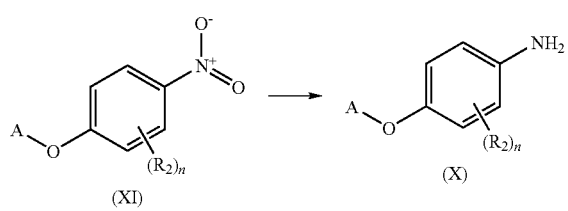

Experimental Procedure 10

Intermediates of formula (XI) can be prepared by art-known procedures by reacting an intermediate of formula (XII) with a suitable hydroxypyridyl intermediate of formula (XIII) such as for example 2-methyl-3-hydroxypyridine according to Reaction Scheme (10). The reaction can be performed in an inert solvent such as, for example, tetrahydrofuran, in the presence of a suitable base such as, for example, cesium carbonate, at moderately elevated temperature such as, for example, 140° C., during for example 16 hours.

In Reaction Scheme (10), all variables are defined as in formula (I).

Reaction Scheme (10)

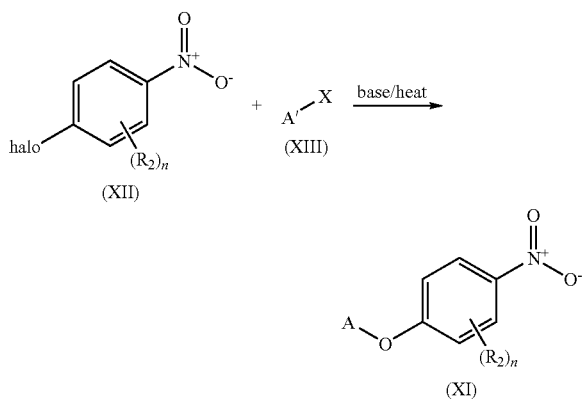

Pharmacology

The compounds provided in this invention are positive allosteric modulators of metabotropic glutamate receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor. Hence, the present invention relates to a compound according to the present invention for use as a medicine, as well as to the use of a compound according to the invention or a pharmaceutical composition according to the invention for the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for use in the manufacture of a medicament for treating or preventing, in particular treating, a condition in a mammal, including a human, the treatment or prevention of which is affected or facilitated by the neuromodulatory effect of allosteric modulators of mGluR2, in particular positive allosteric modulators thereof. The present invention also relates to a compound according to the present invention or a pharmaceutical composition according to the invention for treating or preventing, in particular treating, a condition in a mammal, including a human, the treatment or prevention of which is affected or facilitated by the neuromodulatory effect of allosteric modulators of mGluR2, in particular positive allosteric modulators thereof.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR2.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the present invention relates to the use of a compound of formula (I) for the manufacture of a medicament for treating or preventing, in particular for treating, a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Because such positive allosteric modulators of mGluR2, including compounds of formula (I), enhance the response of mGluR2 to glutamate, it is an advantage that the present methods utilize endogenous glutamate.

Because positive allosteric modulators of mGluR2, including compounds of formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of formula (I), in combination with an mGluR2 agonist.

The compounds of the present invention may be utilized in combination with one or more other drugs in the treatment, prevention, control, amelioration, or reduction of risk of diseases or conditions for which compounds of formula (I) or the other drugs may have utility, where the combination of the drugs together are safer or more effective than either drug alone.

Pharmaceutical Compositions

The invention also relates to a pharmaceutical composition comprising a pharmaceutically acceptable carrier or diluent and, as active ingredient, a therapeutically effective amount of a compound according to the invention, in particular a compound according to formula (I), including a stereochemically isomeric form thereof, or a pharmaceutically acceptable salt thereof or a solvate thereof.

The compounds according to the invention, in particular the compounds according to formula (I), including a stereochemically isomeric form thereof, or a pharmaceutically acceptable salt thereof or a solvate thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The present invention also relates to a combination of a compound according to the present invention and a mGluR2 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR2 orthosteric agonist, as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular positive mGluR2 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Experimental Part

Several methods for preparing the compounds of this invention are illustrated in the following Examples. Unless otherwise noted, all starting materials were obtained from commercial suppliers and used without further purification. Specifically, the following abbreviations may be used in the examples and throughout the specification:

| | |
|---|---|
| EtOAc (ethyl acetate) | HPLC (High Pressure Liquid Chromatography) |
| MeOH (methanol) | DCM (dichloromethane) |
| THF (tetrahydrofuran) | ml (milliliters) |
| min (minutes) | mmol (millimol) |
| DMF (dimethylformamide) | P(=O)Br$_3$ (Phosphoric tribromide) |
| LCMS (Liquid Chromatography Mass Spectrum) | g (grams) |
| Et$_2$O (diethyl ether) | DMSO (dimethylsulfoxide) |

All references to brine refer to a saturated aqueous solution of NaCl. Unless otherwise indicated, all temperatures are expressed in ° C. (degrees Celsius). All reactions are conducted not under an inert atmosphere at room temperature, unless otherwise noted.

Microwave assisted reactions were performed in a single-mode reactor: Emrys™ Optimizer microwave reactor (Personal Chemistry A.B., currently Biotage) or in a multimode reactor: MicroSYNTH Labstation (Milestone, Inc.).

A. PREPARATION OF THE INTERMEDIATES

Example A.1

1-Cyclopropylmethyl-4-methoxy-2-oxo-1,2-dihydro-pyridine-3-carbonitrile (Intermediate 1)

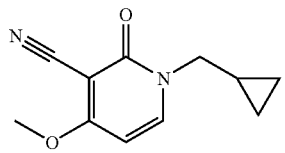

To a solution of 4-methoxy-2-oxo-1,2-dihydro-pyridine-3-carbonitrile (12.2 g, 81.48 mmol) in acetonitrile (250 ml) were added (bromomethyl)cyclopropane (11 g, 81.48 mmol) and potassium carbonate (22.48 g, 162.9 mmol) and the mixture was heated at 110° C. for 24 hours. The mixture was cooled to room temperature and the solid was filtered off. The filtrate was evaporated till dryness and the resulting crude residue was then triturated with diethylether to yield pure intermediate 1 (15.72 g, 94%) as a white solid.

Example A.2

1-Butyl-4-methoxy-2-oxo-1,2-dihydro-pyridine-3-carbonitrile (Intermediate 2)

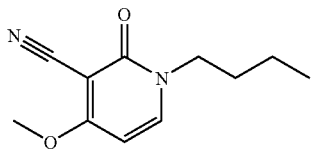

To a solution of 4-methoxy-2-oxo-1,2-dihydro-pyridine-3-carbonitrile (20 g, 133 mmol) in acetonitrile (800 ml) were added 1-bromobutane (15.8 ml, 146 mmol) and potassium carbonate (36.7 g, 266 mmol) and the mixture was heated at 110° C. for 24 hours. The mixture was cooled to room temperature and the solid was filtered off. The filtrate was evaporated till dryness and the resulting crude residue was then triturated with diethylether to yield pure intermediate 2 (27.39 g, >99%) as a white solid.

Example A.3

1-Cyclopropylmethyl-4-hydroxy-2-oxo-1,2-dihydro-pyridine-3-carbonitrile (Intermediate 3)

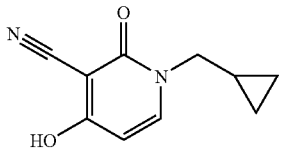

Intermediate 1 (15.7 g, 76.8 mmol) was added at room temperature to a 1N aqueous solution of sodium hydroxide (300 ml) and THF (50 ml). The reaction mixture was heated at 140° C. (oil bath temperature) for 16 hours. The mixture was cooled to room temperature and the THF was mostly evaporated in vacuo. The aqueous layer was cooled to 0° C. and acidified by the addition of aqueous 2N HCl, adjusting the pH to about 3, at which point a white solid precipitated. The solid was filtered off, washed with $Et_2O$ and dried in vacuo to yield intermediate 3 as a white solid (10.44 g, 71%) that was used without further purification.

Example A.4

1-Butyl-4-hydroxy-2-oxo-1,2-dihydro-pyridine-3-carbonitrile (Intermediate 4)

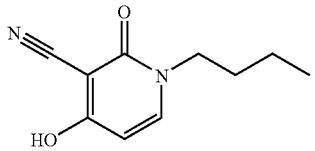

Intermediate 2 (27.39 g, 133 mmol) was added at room temperature to a 1N aqueous solution of sodium hydroxide (500 ml) and THF (100 ml). The reaction mixture was heated at 110° C. (oil bath temperature) for 24 hours. The mixture was cooled to room temperature and the solvent was evaporated in vacuo until the volume was reduced to approximately 250 ml. The aqueous layer was then cooled to 0° C. and acidified by the addition of aqueous 2N HCl, adjusting the pH to about 3, at which point a white solid precipitated. The solid was filtered off, washed with $Et_2O$ and dried in vacuo to yield intermediate 4 as a white solid (25 g, 98%) that was used without further purification.

Example A.5

4-Bromo-1-cyclopropylmethyl-2-oxo-1,2-dihydro-pyridine-3-carbonitrile (Intermediate 5)

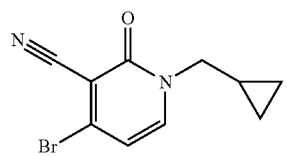

To a solution of intermediate 3 (10.4 g, 54.67 mmol) in DMF (250 ml) was added phosphoric tribromide (31.3 g, 109.3 mmol) and the mixture was heated at 110° C. for 1.5 hours. After cooling in an ice bath the solution was partitioned between water and EtOAc. After three extractions with EtOAc the combined organic fractions were washed with brine, dried over $MgSO_4$ and the solvent evaporated in vacuo. The crude product was purified by column chromatography (silica gel; DCM as eluent). The desired fractions were collected and evaporated in vacuo to yield intermediate 5 (8.83 g, 64%).

Example A.6

4-Bromo-1-butyl-2-oxo-1,2-dihydro-pyridine-3-carbonitrile (Intermediate 6)

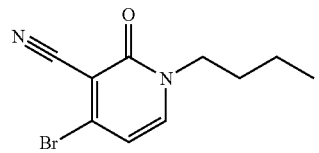

To a solution of intermediate 4 (39 g, 203 mmol) in DMF (600 ml) was added phosphoric tribromide (116 g, 406 mmol) and the mixture was heated at 110° C. for 1.5 hours. After cooling in an ice bath the solution was partitioned between water and EtOAc. After three extractions with EtOAc the combined organic fractions were washed with brine, dried over $Na_2SO_4$ and the solvent evaporated in vacuo. The crude product was purified by column chromatography (silica gel;

DCM as eluent). The desired fractions were collected and evaporated in vacuo to yield intermediate 6 (36.7 g, 72%).

Example A.7

2-(4-Bromo-3-fluoro-phenoxy)-4,6-dimethyl-pyridine (Intermediate 7)

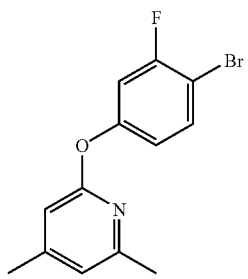

A mixture of 2-bromo-4,6-dimethylpyridine (1 g, 5.4 mmol), 4-bromo-3-fluoro-phenol (1.03 g, 5.4 mmol), and potassium carbonate (0.89 g, 6.4 mmol) was heated at 150° C. (oil bath temperature) in a sealed tube for 7 days. After cooling to room temperature the mixture was diluted with DCM and filtered through a diatomaceous earth pad. The filtrate was evaporated till dryness and the crude product thus obtained was purified by column chromatography (silica gel; DCM as eluent). The desired fractions were collected and evaporated in vacuo to yield intermediate 7 (1.1 g, 53%).

Example A.8

2-[3-Fluoro-4-(4,4,5,5-tetramethyl-[1,3,2]dioxaborolan-2-yl)-phenoxy]-4,6-dimethyl-pyridine (Intermediate 8)

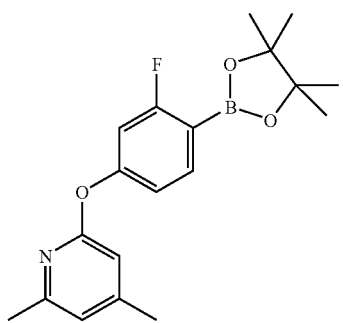

To a solution of intermediate 7 (0.5 g, 1.69 mmol) in 1,4-dioxane (9 ml) and DMF (1 ml) were added bis(pinacolato)diborane (0.643 g, 2.53 mmol) and potassium acetate (0.497 g, 5.06 mmol). The mixture was degassed and then [1,1'-bis(diphenylphosphino)-ferrocene]-dichloropalladium (II); complex with DCM (1:1) (0.0413 g, 0.05 mmol; CAS [95464-05-4]) was added. The reaction mixture was heated at 150° C. for 40 minutes under microwave irradiation. After cooling to room temperature water was added and the mixture was extracted with EtOAc. The organic fraction was dried ($Na_2SO_4$) and the solvent evaporated in vacuo to afford the desired intermediate 8 (0.6 g, 100%) as a crude product that was used without further purification.

Example A.9

3-(2-Fluoro-4-nitro-phenoxy)-2,6-dimethyl-pyridine (Intermediate 9)

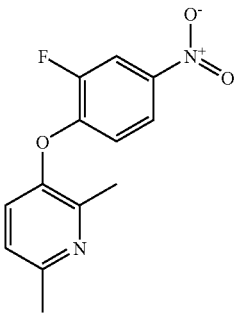

To a room temperature solution of 2,6-dimethyl-3-pyridinol (3 g, 24.35 mmol) in THF (30 ml) was added cesium carbonate (15.87 g, 48.71 mmol) and 3,4-difluoro-1-nitrobenzene (3.87 g, 24.35 mmol). The reaction mixture was heated at reflux for 2 hours. After cooling to room temperature the solids were filtered off and the filtrate was evaporated till dryness. The crude product was purified by column chromatography (silica gel; DCM to DCM/MeOH($NH_3$) up to 2% as eluent). The desired fractions were collected and evaporated in vacuo to yield intermediate 9 (5.88 g, 92%).

Example A.10

4-(2,6-Dimethyl-pyridin-3-yloxy)-3-fluoro-phenylamine (Intermediate 10)

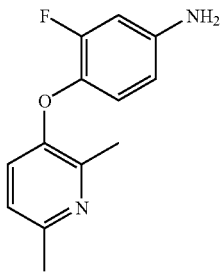

A solution of intermediate 9 (5.88 g, 22.44 mmol) in ethanol (200 ml) was hydrogenated at room temperature in the presence of palladium 10% on activated carbon (0.58 g) for 3 hours. The solids were filtered off and the filtrate was evaporated till dryness to yield intermediate 10 (5.20 g, >99%) that was used without further purification.

Example A.11

3-(4-Bromo-2-fluoro-phenoxy)-2,6-dimethyl-pyridine (Intermediate 11)

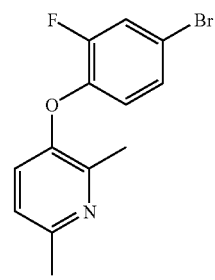

To a solution of intermediate 10 (7.7 g, 33.2 mmol) in HBr (75 ml, 48% aqueous), cooled to 0° C., a solution of sodium nitrite (4.57 g, 66.3 mmol) in water (75 ml) was dropwise added over 45 minutes. The reaction mixture was warmed to room temperature and further stirred for 15 minutes. The mixture was cooled to 0° C. and copper (I) bromide (4.0 g, 28.4 mmol) was added portionwise. Stirring was continued for 15 minutes at 0° C. and then the mixture was warmed to room temperature and further stirred for 15 minutes. The reaction mixture was then heated at 140° C. for 1.5 hours. The mixture was cooled to room temperature and carefully neutralized with an aqueous saturated solution of potassium carbonate. EtOAc was then added and layers were separated. The organic phase was dried (Na$_2$SO$_4$) and evaporated till dryness. The crude product was purified by column chromatography (silica gel; heptane to heptane/EtOAc up to 10% as eluent). The desired fractions were collected and evaporated in vacuo to yield intermediate 11 (8.75 g, 89%).

Example A.12

3-[2-Fluoro-4-(4,4,5,5-tetramethyl-[1,3,2]dioxaborolan-2-yl)-phenoxy]-2,6-dimethyl-pyridine (Intermediate 12)

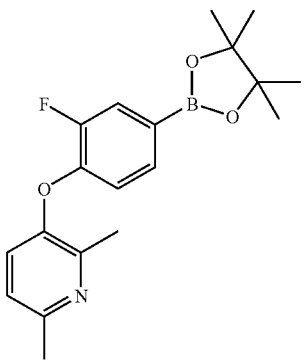

To a solution of intermediate 11 (1.5 g, 5.07 mmol) in 1,4-dioxane (9 ml) and DMF (3 ml) were added bis(pinacolato)diborane (3.86 g, 15.2 mmol) and potassium acetate (1.48 g, 15.2 mmol). The mixture was degassed and then [1,1'-bis(diphenylphosphino)-ferrocene]-dichloropalladium (II); complex with DCM (1:1) (0.16 g, 0.20 mmol; CAS [95464-05-4]) was added. The reaction mixture was heated at 150° C. for 10 minutes under microwave irradiation. After cooling to room temperature water was added and the mixture was extracted with EtOAc. The organic fraction was dried (Na$_2$SO$_4$) and the solvent evaporated in vacuo to afford the desired boronate intermediate 12 (1.74 g, 100%) as a crude product that was used without further purification.

Example A.13

4-(4-Bromo-3-fluoro-phenoxy)-2-methyl-pyridine 1-oxide (Intermediate 13)

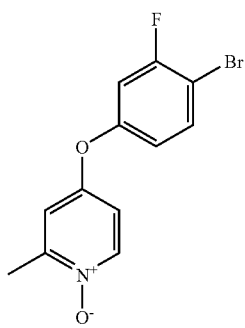

To a room temperature solution of 4-bromo-3-fluorophenol (6 g, 31.41 mmol) in N-methylpyrrolidone (20 ml) was added sodium hydride (1.34 g, 56 mmol, 60% in mineral oil) portionwise. After stirring for 10 minutes 4-nitro-2-picoline N-oxide (5.6 g, 36.12 mmol) was added. The reaction mixture was heated at 180° C. for 60 minutes under microwave irradiation. After cooling to room temperature the mixture was diluted with EtOAc (250 ml) and washed with water (250 ml). The solution was then extracted with additional EtOAc (2×150 ml). The combined organic extracts were dried (Na$_2$SO$_4$) and the solvent evaporated in vacuo. The crude product was purified by column chromatography (silica gel; DCM to DCM/MeOH(NH$_3$) up to 2% as eluent). The desired fractions were collected and evaporated in vacuo to yield intermediate 13 (3.61 g, 39%).

Example A.14

2-Fluoro-4-(2-methyl-4-pyridyloxy)phenyl boronic acid (Intermediate 14)

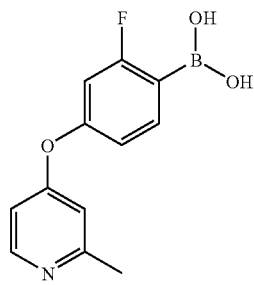

To a solution of intermediate 13 (1.05 g, 3.52 mmol) in 1,4-dioxane (9 ml) and DMF (4 ml) were added bis(pinacolato)diborane (2.68 g, 10.56 mmol) and potassium acetate (1.035 g, 10.56 mmol). The mixture was degassed and then [1,1'-bis(diphenylphosphino)-ferrocene]-dichloropalladium (II); complex with DCM (1:1) (0.115 g, 0.141 mmol; CAS [95464-05-4]) was added. The reaction mixture was heated at 150° C. for 15 minutes under microwave irradiation. After cooling to room temperature water was added and the mixture was extracted with EtOAc (20 ml). The organic fraction was dried (Na$_2$SO$_4$) and the solvent evaporated in vacuo to afford the desired boronate intermediate 14 (0.87 g, 100%) as a crude product that was used without further purification.

Example A.15

4-(4-Bromo-2-fluoro-phenoxy)-2-methyl-pyridine 1-oxide (Intermediate 15)

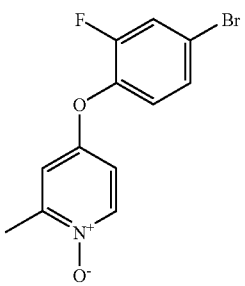

To a room temperature solution of 4-bromo-2-fluorophenol (3.44 ml, 31.41 mmol) in N-methylpyrrolidone (20 ml) was added sodium hydride (1.34 g, 56 mmol, 60% in mineral oil) portionwise. After stirring for 20 minutes 4-nitro-2-picoline N-oxide (5.6 g, 36.12 mmol) was added The reaction mixture was heated at 180° C. for 60 minutes under microwave irradiation. After cooling to room temperature the mixture was diluted with EtOAc (250 ml) and washed with water (250 ml). The solution was then extracted with additional EtOAc (2×150 ml). The combined organic extracts were dried (Na$_2$SO$_4$) and the solvent evaporated in vacuo. The crude product was purified by column chromatography (silica gel; DCM to DCM/MeOH(NH$_3$) up to 2% as eluent). The desired fractions were collected and evaporated in vacuo to yield intermediate 15 (4.36 g, 47%).

Example A.16

3-Fluoro-4-(2-methyl-4-pyridyloxy)phenyl boronic acid (Intermediate 16)

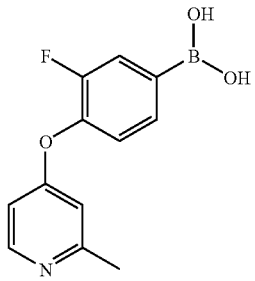

To a solution of intermediate 15 (1.05 g, 3.52 mmol) in 1,4-dioxane (9 ml) and DMF (4 ml) were added bis(pinacolato)diborane (2.68 g, 10.56 mmol) and potassium acetate (1.035 g, 10.56 mmol). The mixture was degassed and then [1,1'-bis(diphenylphosphino)-ferrocene]-dichloropalladium (II); complex with DCM (1:1) (0.115 g, 0.141 mmol; CAS [95464-05-4]) was added. The reaction mixture was heated at 150° C. for 15 minutes under microwave irradiation. After cooling to room temperature water was added and the mixture was extracted with EtOAc (20 ml). The organic fraction was dried (Na$_2$SO$_4$) and the solvent evaporated in vacuo to afford the desired boronate intermediate 16 (0.87 g, 100%) as a crude product that was used without further purification.

Example A.17

4-(4-Bromo-3-fluoro-phenoxy)-2,6-dimethyl-pyridine (Intermediate 17)

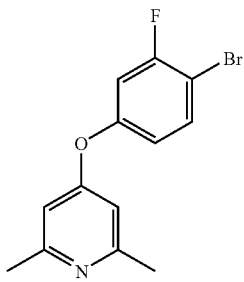

A mixture of 4-bromo-2,6-dimethyl-pyridine (1 g, 5.4 mmol), 4-bromo-3-fluoro-phenol (0.59 g, 5.4 mmol), and potassium carbonate (0.89 g, 6.4 mmol) in xylenes (2 ml) was heated at 150° C. (oil bath temperature) in a sealed tube for 48 hours. After cooling to room temperature the mixture was diluted with EtOAc and filtered through a diatomaceous earth pad. The filtrate was evaporated till dryness and the crude product thus obtained was purified by column chromatography (silica gel; DCM to DCM/EtOAc up to 10% as eluent). The desired fractions were collected and evaporated in vacuo to yield intermediate 17 (1.18 g, 72%).

Example A.18

4-[3-Fluoro-4-(4,4,5,5-tetramethyl-[1,3,2]dioxaborolan-2-yl)-phenoxy]-2,6-dimethyl-pyridine (Intermediate 18)

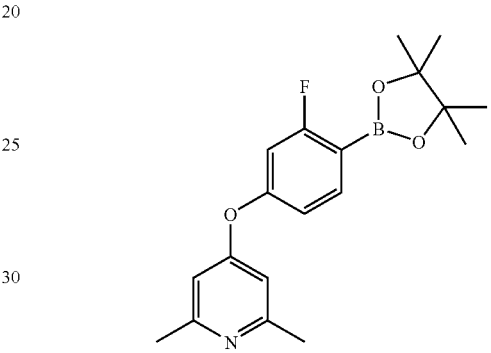

To a solution of intermediate 17 (1 g, 3.37 mmol) in 1,4-dioxane (10.8 ml) and DMF (1.2 ml) were added bis(pinacolato)diborane (1.286 g, 5.06 mmol) and potassium acetate (0.994 g, 10.13 mmol). The mixture was degassed and then [1,1'-bis(diphenylphosphino)-ferrocene]-dichloropalladium (II); complex with DCM (1:1) (0.0827 g, 0.101 mmol; CAS [95464-05-4]) was added. The reaction mixture was heated at 150° C. for 10 minutes under microwave irradiation. After cooling to room temperature water was added and the mixture was extracted with EtOAc. The organic fraction was dried (Na$_2$SO$_4$) and the solvent evaporated in vacuo to afford the desired boronate intermediate 18 (1.14 g, 100%) as a crude product that was used without further purification.

Example A.19

4-(4-Bromo-2-fluoro-phenoxy)-2,6-dimethyl-pyridine (Intermediate 19)

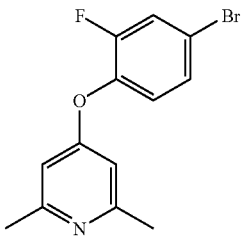

A mixture of 4-bromo-2,6-dimethyl-pyridine (1 g, 5.4 mmol), 4-bromo-2-fluoro-phenol (0.59 g, 5.4 mmol), and potassium carbonate (0.89 g, 6.4 mmol) in xylenes (2 ml) was heated at 150° C. (oil bath temperature) in a sealed tube for 48 hours. After cooling to room temperature the mixture was diluted with EtOAc and filtered through a diatomaceous earth pad. The filtrate was evaporated till dryness and the crude product thus obtained was purified by column chromatography (silica gel; DCM to DCM/EtOAc up to 10% as eluent). The desired fractions were collected and evaporated in vacuo to yield intermediate 19 (1.28 g, 80%).

Example A.20

4-[2-Fluoro-4-(4,4,5,5-tetramethyl-[1,3,2]dioxaborolan-2-yl)-phenoxy]-2,6-dimethyl-pyridine (Intermediate 20)

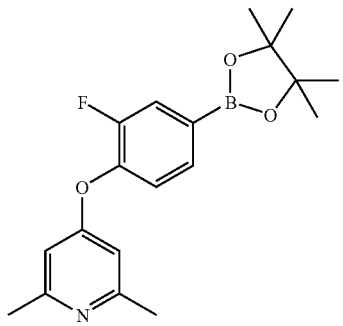

To a solution of intermediate 19 (1 g, 3.37 mmol) in 1,4-dioxane (10.8 ml) and DMF (1.2 ml) were added bis(pinacolato)diborane (1.286 g, 5.06 mmol) and potassium acetate (0.994 g, 10.13 mmol). The mixture was degassed and then [1,1'-bis(diphenylphosphino)-ferrocene]-dichloropalladium (II); complex with DCM (1:1) (0.0827 g, 0.101 mmol; CAS [95464-05-4]) was added. The reaction mixture was heated at 150° C. for 10 minutes under microwave irradiation. After cooling to room temperature water was added and the mixture was extracted with EtOAc. The organic fraction was dried ($Na_2SO_4$) and the solvent evaporated in vacuo to afford the desired boronate intermediate 20 (1.15 g, 100%) as a crude product that was used without further purification.

Example A.21

4-(4-Bromo-3-fluoro-phenoxy)-2,3-dimethyl-pyridine 1-oxide (Intermediate 21)

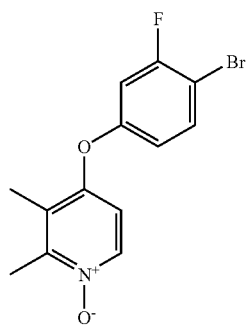

To a room temperature solution of 4-bromo-3-fluorophenol (15 g, 78.53 mmol) in DMF (50 ml) was added sodium hydride (3.32 g, 85.67 mmol, 60% in mineral oil) portionwise. After stirring for 10 minutes 2,3-dimethyl-4-nitro-pyridine 1-oxide (1.05 g, 6.28 mmol) was added The reaction mixture was heated at 180° C. for 60 minutes under microwave irradiation. After cooling to room temperature the mixture was filtered through a diatomaceous earth pad and the filtrate was then diluted with EtOAc and washed with water. The solution was then extracted with additional EtOAc (2×150 ml). The organic layer was dried ($Na_2SO_4$) and the solvent evaporated in vacuo. The crude product was purified by column chromatography (silica gel; DCM to DCM/MeOH up to 5% as eluent). The desired fractions were collected and evaporated in vacuo to yield intermediate 21 (3.44 g, 19%).

Example A.22

2-Fluoro-4-(2,3-dimethyl-4-pyridyloxy)phenylboronic acid (Intermediate 22)

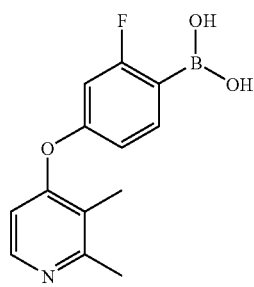

To a solution of intermediate 21 (0.40 g, 1.28 mmol) in 1,4-dioxane (2.6 ml) and DMF (0.8 ml) were added bis(pinacolato)diborane (0.97 g, 3.84 mmol) and potassium acetate (0.37 g, 3.84 mmol). The mixture was degassed and then [1,1'-bis(diphenylphosphino)-ferrocene]-dichloropalladium (II); complex with DCM (1:1) (0.042 g, 0.051 mmol; CAS [95464-05-4]) was added. The reaction mixture was heated at 150° C. for 15 minutes under microwave irradiation. After cooling to room temperature water was added and the mixture was extracted with EtOAc. The organic fraction was dried ($Na_2SO_4$) and the solvent evaporated in vacuo to afford the desired boronate intermediate 22 (0.334 g, 100%) as a crude product that was used without further purification.

Example A.23

4-(4-Bromo-2-fluoro-phenoxy)-2,3-dimethyl-pyridine 1-oxide (Intermediate 23)

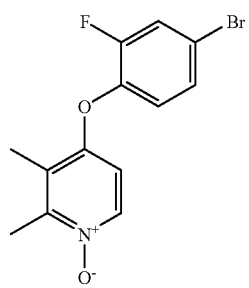

To a room temperature solution of 4-bromo-2-fluorophenol (1 g, 5.23 mmol) in N-methylpyrrolidone (10 ml) was added sodium hydride (0.27 g, 6.79 mmol, 60% in mineral oil) portionwise. After stirring for 10 minutes 2,3-dimethyl-4-nitro-pyridine 1-oxide (1.05 g, 6.28 mmol) was added The reaction mixture was heated at 180° C. for 60 minutes under microwave irradiation. After cooling to room temperature the mixture was filtered through a diatomaceous earth pad and the filtrate was then diluted with EtOAc and washed with water. The solution was then extracted with additional EtOAc (2×150 ml). The organic layer was dried ($Na_2SO_4$) and the solvent evaporated in vacuo. The crude product was purified by column chromatography (silica gel; DCM to DCM/MeOH up to 3% as eluent). The desired fractions were collected and evaporated in vacuo to yield intermediate 23 (0.75 g, 46%).

Example A.24

4-[2-Fluoro-4-(4,4,5,5-tetramethyl-[1,3,2]dioxaborolan-2-yl)-phenoxy]-2,3-dimethyl-pyridine (Intermediate 24)

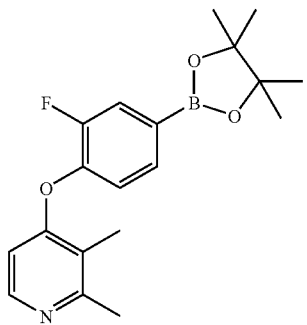

To a solution of intermediate 23 (0.420 g, 1.36 mmol) in 1,4-dioxane (6 ml) and DMF (2 ml) were added bis(pinacolato)diborane (1.025 g, 4.03 mmol) and potassium acetate (0.385 g, 4.03 mmol). The mixture was degassed and then [1,1'-bis(diphenylphosphino)-ferrocene]-dichloropalladium (II); complex with DCM (1:1) (0.044 g, 0.054 mmol; CAS [95464-05-4]) was added. The reaction mixture was heated at 150° C. for 10 minutes under microwave irradiation. After cooling to room temperature water was added and the mixture was extracted with EtOAc. The organic fraction was dried ($Na_2SO_4$) and the solvent evaporated in vacuo to afford the desired boronate intermediate 24 (1.41 g, 100%) as a crude product that was used without further purification.

Example A.25

4-(4-Bromo-phenoxy)-2-methyl-pyridine (Intermediate 25)

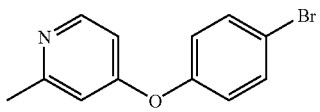

To a solution of NaH (60% in mineral oil) (0.13 g, 3.25 mmol) in DMF (5 ml) was added commercially available 4-bromophenol (0.50 g, 2.89 mmol) and the reaction was stirred at room temperature for 10 minutes. Then, 4-chloro-2-picoline (0.30 g, 2.40 mmol) was added and the resulting reaction mixture was then microwaved at 150° C. for 10 minutes. After cooling, the mixture was diluted with water and extracted with $Et_2O$. The combined organic layers were dried over $Na_2SO_4$ and concentrated in vacuo. The residue thus obtained was purified by flash chromatography (DCM) to yield intermediate 25 (0.52 g, 81%).

Example A.26

4-[4-(4,4,5,5-tetramethyl-[1,3,2]dioxaborolan-2-yl)-phenoxy]-2-methyl-pyridine (Intermediate 26)

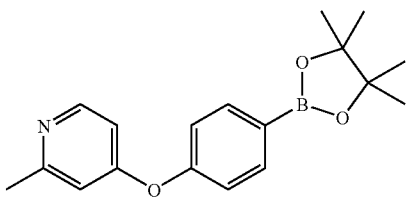

To a solution of intermediate 25 (0.50 g, 1.89 mmol) in DMSO (5 ml) was added bis(pinacolato)diboron (0.72 g, 2.84 mmol) and KOAc (0.56 g, 5.68 mmol), the solution was then degassed using a stream of nitrogen and then to the reaction mixture was added 1,1'-bis(diphenylphosphino)ferrocene-palladium (II) dichloride, DCM (0.05 g, 0.06 mmol). The reaction mixture was then heated at 110° C. under a nitrogen atmosphere for 16 hours. The reaction was then cooled to room temperature and diluted with water and the resulting solution was extracted with AcOEt. The organic fraction was then dried over $Na_2SO_4$ and concentrated in vacuo to yield intermediate 26 (0.58 g, 100%) used in the next reaction step without further purification.

B. PREPARATION OF THE FINAL COMPOUNDS

Example B.1

1-Cyclopropylmethyl-4-[4-(4,6-dimethyl-pyridin-2-yloxy)-2-fluoro-phenyl]-2-oxo-1,2-dihydro-pyridine-3-carbonitrile (Compound 1)

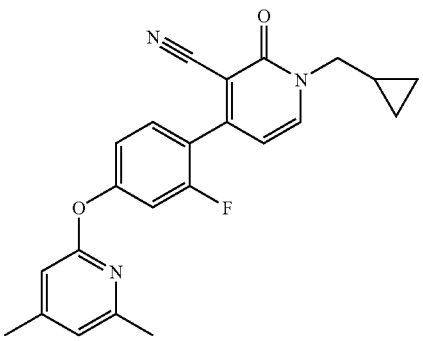

To a solution of intermediate 8 (1.42 mmol) in 1,4-dioxane (6 ml) and a saturated solution of $NaHCO_3$ (5 ml) was added intermediate 5 (0.329 g, 1.3 mmol). The resulting solution was degassed using a stream of nitrogen and to this was added Pd(PPh$_3$)$_4$ (0.15 mg, 0.13 mmol). The reaction was then microwaved in a sealed tube at 140° C. for 5 minutes. The resulting cooled reaction mixture was then diluted with EtOAc and filtered through a pad of diatomaceous earth. The filtrate was washed with water, dried (Na$_2$SO$_4$) and concentrated in vacuo. The crude reaction mixture was then purified by column chromatography (silica gel; DCM to DCM/EtOAc up to 10% as eluent). The desired fractions were collected and evaporated in vacuo to yield compound 1 that was washed with diethyleter and dried in vacuum (0.207 g, 41%). Melting point: 137.0° C.

Example B.2

1-Butyl-4-[4-(2,6-dimethyl-pyridin-3-yloxy)-3-fluoro-phenyl]-2-oxo-1,2-dihydro-pyridine-3-carbonitrile (Compound 2)

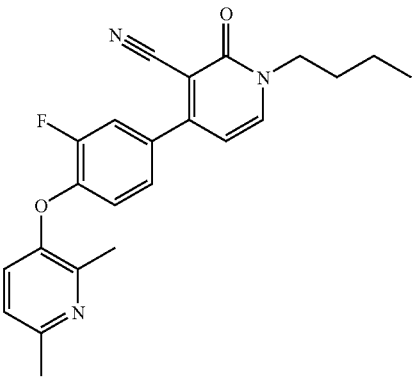

To a solution of intermediate 12 (2 mmol) in 1,4-dioxane (6 ml) and a saturated solution of NaHCO$_3$ (6 ml) was added intermediate 6 (0.51 g, 2 mmol). The resulting solution was degassed using a stream of nitrogen and to this was added Pd(PPh$_3$)$_4$ (0.231 mg, 0.2 mmol). The reaction was then microwaved in a sealed tube at 150° C. for 10 minutes. The resulting cooled reaction mixture was filtered through a pad of diatomaceous earth and concentrated in vacuo. The crude reaction mixture was then purified by column chromatography (silica gel; DCM to DCM/MeOH up to 3% as eluent). The desired fractions were collected and evaporated in vacuo to yield compound 2 (0.405 g, 52%).

Melting point: 156.4° C.

Compounds 12, 14 and 16 (see Table 1) can be prepared according to the protocol described for compound 2.

Example B.3

1-Cyclopropylmethyl-4-[4-(2,6-dimethyl-pyridin-3-yloxy)-3-fluoro-phenyl]-2-oxo-1,2-dihydro-pyridine-3-carbonitrile (Compound 3)

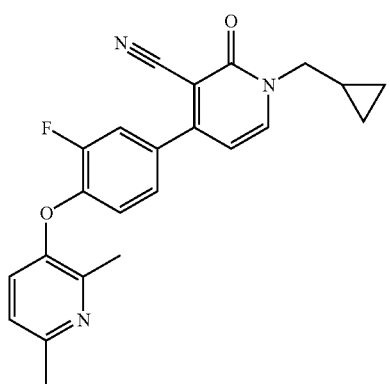

To a solution of intermediate 12 (2 mmol) in 1,4-dioxane (6 ml) and a saturated solution of NaHCO$_3$ (6 ml) was added intermediate 5 (0.51 g, 2 mmol). The resulting solution was degassed using a stream of nitrogen and to this was added Pd(PPh$_3$)$_4$ (0.231 mg, 0.2 mmol). The reaction was then microwaved in a sealed tube at 150° C. for 10 minutes. The resulting cooled reaction mixture was filtered through a pad of diatomaceous earth and concentrated in vacuo. The crude reaction mixture was then purified by column chromatography (silica gel; DCM to DCM/MeOH up to 3% as eluent). The desired fractions were collected and evaporated in vacuo to yield compound 3 (0.445 g, 58%).

Melting point: 152.7° C.

Example B.4

1-Butyl-4-[2-fluoro-4-(2-methyl-pyridin-4-yloxy)-phenyl]-2-oxo-1,2-dihydro-pyridine-3-carbonitrile (Compound 4)

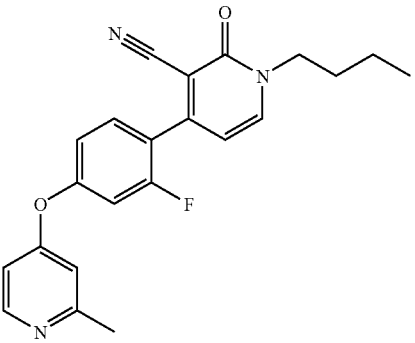

To a solution of intermediate 14 (1.77 mmol) in 1,4-dioxane (6 ml) and a saturated solution of NaHCO$_3$ (6 ml) was added intermediate 6 (0.451 g, 1.77 mmol). The resulting solution was degassed using a stream of nitrogen and to this was added Pd(PPh$_3$)$_4$ (0.204 mg, 0.177 mmol). The reaction was then microwaved in a sealed tube at 150° C. for 10 minutes. The resulting cooled reaction mixture was filtered through a pad of diatomaceous earth and concentrated in vacuo. The crude reaction mixture was then purified by column chromatography (silica gel; DCM to DCM/MeOH up to 3% as eluent). The desired fractions were collected and evaporated in vacuo to yield compound 4 (0.45 g, 68%).

Melting point: 127.1° C.

Compounds 13, 17, 19 and 20 (see Table 1) can be prepared according to the protocol described for compound 4.

Example B.5

1-Butyl-4-[3-fluoro-4-(2-methyl-pyridin-4-yloxy)-phenyl]-2-oxo-1,2-dihydro-pyridine-3-carbonitrile (Compound 5)

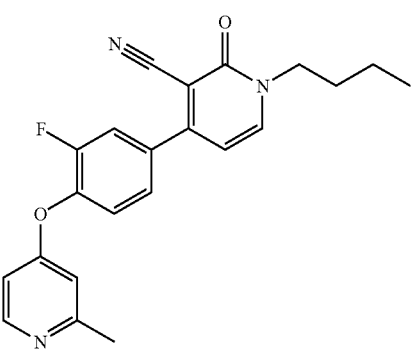

To a solution of intermediate 16 (1.77 mmol) in 1,4-dioxane (6 ml) and a saturated solution of NaHCO$_3$ (6 ml) was added intermediate 6 (0.451 g, 1.77 mmol). The resulting solution was degassed using a stream of nitrogen and to this was added Pd(PPh$_3$)$_4$ (0.204 mg, 0.177 mmol). The reaction was then microwaved in a sealed tube at 150° C. for 10 minutes. The resulting cooled reaction mixture was filtered through a pad of diatomaceous earth and concentrated in vacuo. The crude reaction mixture was then purified by column chromatography (silica gel; DCM to DCM/MeOH up to 3% as eluent). The desired fractions were collected and evaporated in vacuo to yield compound 5 (0.45 g, 68%).
Melting point: 125.4° C.

Compound 15 (see Table 1) can be prepared according to the protocol described for compound 5.

Example B.6

1-Butyl-4-[4-(2,6-dimethyl-pyridin-4-yloxy)-2-fluoro-phenyl]-2-oxo-1,2-dihydro-pyridine-3-carbonitrile (Compound 6)

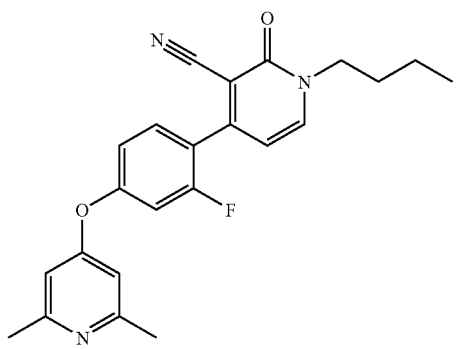

To a solution of intermediate 18 (1.078 mmol) in 1,4-dioxane (6 ml) and a saturated solution of NaHCO$_3$ (5 ml) was added intermediate 6 (0.25 g, 0.979 mmol). The resulting solution was degassed using a stream of nitrogen and to this was added Pd(PPh$_3$)$_4$ (0.113 mg, 0.098 mmol). The reaction was then microwaved in a sealed tube at 150° C. for 10 minutes. The resulting cooled reaction mixture was filtered through a pad of diatomaceous earth and the pad of diatomaceous earth was washed with EtOAc. The combined filtrates were washed with water and the organic layer was separated, dried (Na$_2$SO$_4$) and concentrated in vacuo. The crude reaction mixture was then purified by column chromatography (silica gel; DCM to DCM/MeOH up to 2% as eluent). The desired fractions were collected and evaporated in vacuo to yield compound 6 that was precipitated from diethylether (0.220 g, 57%).
Melting point: 169.9° C.

Example B.7

1-Butyl-4-[4-(2,6-dimethyl-pyridin-4-yloxy)-3-fluoro-phenyl]-2-oxo-1,2-dihydro-pyridine-3-carbonitrile (Compound 7)

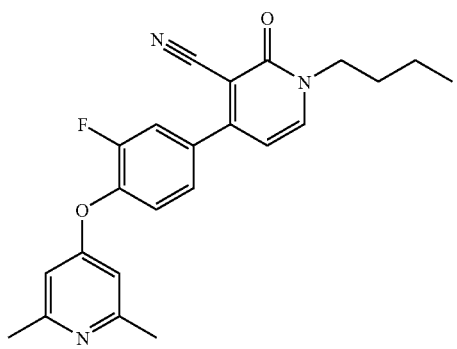

To a solution of intermediate 20 (1.078 mmol) in 1,4-dioxane (6 ml) and a saturated solution of NaHCO$_3$ (5 ml) was added intermediate 6 (0.25 g, 0.979 mmol). The resulting solution was degassed using a stream of nitrogen and to this was added Pd(PPh$_3$)$_4$ (0.113 mg, 0.098 mmol). The reaction was then microwaved in a sealed tube at 150° C. for 10 minutes. The resulting cooled reaction mixture was filtered through a pad of diatomaceous earth and the pad of diatomaceous earth was washed with EtOAc.

The combined filtrates were washed with water and the organic layer was separated, dried (Na$_2$SO$_4$) and concentrated in vacuo. The crude reaction mixture was then purified by column chromatography (silica gel; DCM to DCM/MeOH up to 2% as eluent). The desired fractions were collected and evaporated in vacuo to yield compound 7 that was precipitated from diethylether (0.225 g, 59%).

Melting point: 205.4° C.

Example B.8

1-Cyclopropylmethyl-4-[4-(2,6-dimethyl-pyridin-4-yloxy)-2-fluoro-phenyl]-2-oxo-1,2-dihydro-pyridine-3-carbonitrile (Compound 8)

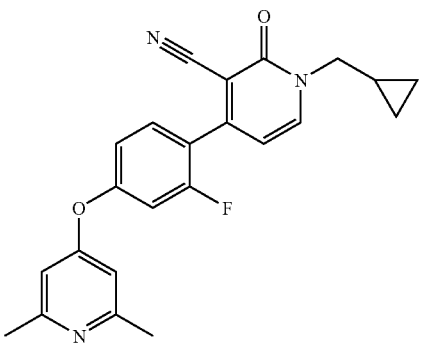

To a solution of intermediate 18 (1.05 mmol) in 1,4-dioxane (4.5 ml) and a saturated solution of NaHCO$_3$ (4.5 ml) was added intermediate 5 (0.22 g, 0.892 mmol). The resulting solution was degassed using a stream of nitrogen and to this was added Pd(PPh$_3$)$_4$ (0.13 mg, 0.114 mmol). The reaction was then microwaved in a sealed tube at 150° C. for 10 minutes. The resulting cooled reaction mixture was filtered through a pad of diatomaceous earth. The filtrate was diluted with EtOAc, and then it was washed with water, dried over Na$_2$SO$_4$ and concentrated in vacuo. The crude reaction mixture was then purified by column chromatography (silica gel; DCM to DCM/MeOH up to 5% as eluent). The desired fractions were collected and evaporated in vacuo to give a residue that was further purified by column chromatography (silica gel; DCM to DCM/EtOAc up to 10% as eluent). The desired fractions were collected and evaporated in vacuo to yield compound 8 that was precipitated from diisopropylether (0.176 g, 51%).

Melting point: decomposed

Example B.9

1-Cyclopropylmethyl-4-[4-(2,6-dimethyl-pyridin-4-yloxy)-3-fluoro-phenyl]-2-oxo-1,2-dihydro-pyridine-3-carbonitrile (Compound 9)

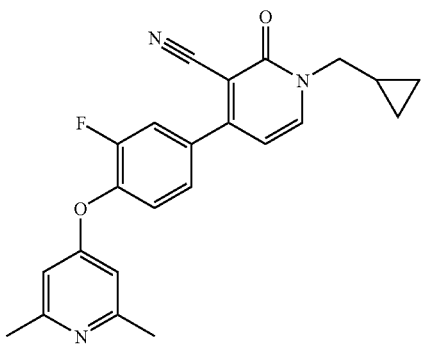

To a solution of intermediate 20 (1.066 mmol) in 1,4-dioxane (4.5 ml) and a saturated solution of NaHCO$_3$ (4.5 ml) was added intermediate 5 (0.23 g, 0.906 mmol). The resulting solution was degassed using a stream of nitrogen and to this was added Pd(PPh$_3$)$_4$ (0.12 mg, 0.106 mmol). The reaction was then microwaved in a sealed tube at 150° C. for 10 minutes. The resulting cooled reaction mixture was filtered through a pad of diatomaceous earth. The filtrate was diluted with EtOAc, and then it was washed with water, dried (Na$_2$SO$_4$) and concentrated in vacuo. The crude reaction mixture was then purified by column chromatography (silica gel; DCM to DCM/EtOAc up to 50% as eluent). The desired fractions were collected and evaporated in vacuo to yield compound 9 that was precipitated from diethylether (0.144 g, 42%).

Melting point: 201.2° C.

Example B.10

1-Cyclopropylmethyl-4-[4-(2,3-dimethyl-pyridin-4-yloxy)-2-fluoro-phenyl]-2-oxo-1,2-dihydro-pyridine-3-carbonitrile (Compound 10)

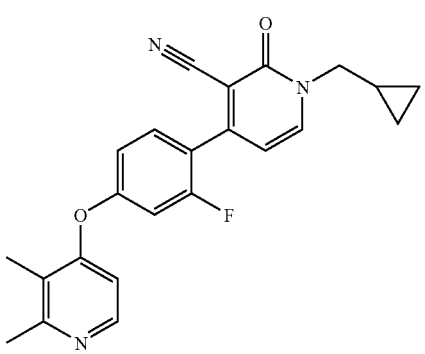

To a solution of intermediate 22 (0.34 g 1.321 mmol) in 1,4-dioxane (5.5 ml) and a saturated solution of NaHCO$_3$ (5.5 ml) was added intermediate 5 (0.28 g, 1.123 mmol). The resulting solution was degassed using a stream of nitrogen and to this was added Pd(PPh$_3$)$_4$ (0.15 mg, 0.132 mmol). The reaction was then microwaved in a sealed tube at 150° C. for 10 minutes. The resulting cooled reaction mixture was filtered through a pad of diatomaceous earth. The filtrate was diluted with EtOAc, and then it was washed with water, dried (Na$_2$SO$_4$) and concentrated in vacuo. The crude reaction mixture was then purified by column chromatography (silica gel; DCM to DCM/AcOEt 1:1 as eluent). The desired fractions were collected and evaporated in vacuo to give a residue that was triturated with Et$_2$O to yield compound 10 (0.068 g, 16%)

Example B.11

1-Cyclopropylmethyl-4-[4-(2,3-dimethyl-pyridin-4-yloxy)-3-fluoro-phenyl]-2-oxo-1,2-dihydro-pyridine-3-carbonitrile (Compound 11)

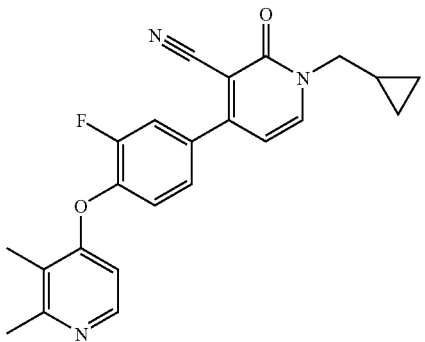

To a solution of intermediate 24 (1.769 mmol) in 1,4-dioxane (7 ml) and a saturated solution of NaHCO$_3$ (7 ml) was added intermediate 5 (0.38 g, 1.504 mmol). The resulting solution was degassed using a stream of nitrogen and to this was added Pd(PPh$_3$)$_4$ (0.2 mg, 0.176 mmol). The reaction was then microwaved in a sealed tube at 150° C. for 10 minutes. The resulting cooled reaction mixture was filtered through a pad of diatomaceous earth. The filtrate was diluted with EtOAc, and then it was washed with water, dried (Na$_2$SO$_4$) and concentrated in vacuo. The crude reaction mixture was then purified by column chromatography (silica gel; DCM to DCM/MeOH up to 5% as eluent). The desired fractions were collected and evaporated in vacuo to yield compound 11 precipitated from diisopropylether (0.190 g, 32%).

Melting point: decomposed

Example B.12

3-cyano-1-butyl-4-[4-(2-methyl-pyridin-4-yloxy)-phenyl]-pyridine-2(1H)-one (Compound 18)

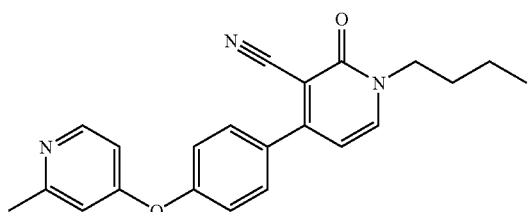

Intermediate 6 (0.48 g, 1.89 mmol) and intermediate 26 (0.59 g, 1.89 mmol) were mixed in 1,4-dioxane (4 ml) and a saturated solution of NaHCO$_3$ (4 ml). The resulting solution was degassed using a stream of nitrogen and to this was added Pd(PPh$_3$)$_4$ (0.22 g, 0.19 mmol). The reaction was then microwaved into a sealed tube at 150° C. for 10 minutes. The resulting reaction mixture was then filtered through a pad of diatomaceous earth and washed with AcOEt. The filtrate was washed with brine. The combined organic layers were dried over MgSO$_4$ and concentrated in vacuo. The residue thus obtained was purified by flash chromatography (DCM/MeOH mixtures) to yield compound 18 (0.16 g, 25%).

Table 1 lists compounds of formula (I) that were prepared according to one of the above Examples (Ex. no.).

TABLE 1

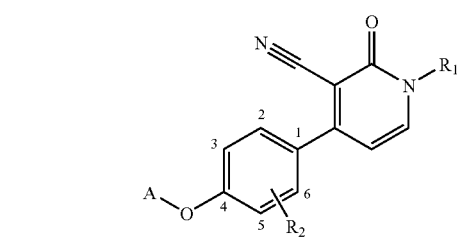

| Comp. no. | Ex. no. | ----R$_1$ | R$^2$ | ----A |
|---|---|---|---|---|
| 1 | B1 | cyclopropyl | 2-F | 2,6-dimethylpyridin-4-yl |
| 2 | B2 | butyl | 3-F | 2,6-dimethylpyridin-3-yl |
| 3 | B3 | cyclopropylmethyl | 3-F | 2,6-dimethylpyridin-3-yl |
| 4 | B4 | butyl | 2-F | 2-methylpyridin-4-yl |
| 5 | B5 | butyl | 3-F | 2-methylpyridin-4-yl |
| 6 | B6 | butyl | 2-F | 2,6-dimethylpyridin-4-yl |
| 7 | B7 | butyl | 3-F | 2,6-dimethylpyridin-4-yl |

TABLE 1-continued

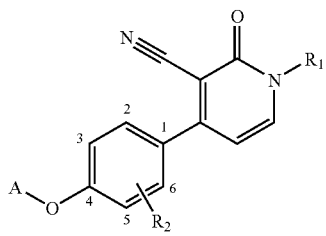

| Comp. no. | Ex. no. | ----R$_1$ | R$^2$ | ----A |
|---|---|---|---|---|
| 8 | B8 | cyclopropylmethyl | 2-F | 2,6-dimethylpyridin-3-yl |
| 9 | B9 | cyclopropylmethyl | 3-F | 2,6-dimethylpyridin-3-yl |
| 10 | B10 | cyclopropylmethyl | 2-F | 2,3-dimethylpyridin-4-yl |
| 11 | B11 | cyclopropylmethyl | 3-F | 2,3-dimethylpyridin-4-yl |
| 12 | B2 | butyl | 3-F | 2-methylpyridin-3-yl |
| 13 | B4 | cyclopropylmethyl | 2-F | 2-methylpyridin-4-yl |
| 14 | B2 | cyclopropylmethyl | 3-F | 2-methylpyridin-3-yl |
| 15 | B5 | butyl | 3,5-diF | 2-methylpyridin-4-yl |
| 16 | B2 | butyl | H | 2-methylpyridin-3-yl |
| 17 | B4 | butyl | H | 2-methylpyridin-4-yl |

TABLE 1-continued

| Comp. no. | Ex. no. | ----R₁ | R² | ----A |
|---|---|---|---|---|
| 18 | B12 | n-butyl | H | 2-methylpyridin-4-yl |
| 19 | B4 | cyclopropylmethyl | H | 2-chloropyridin-4-yl |
| 20 | B4 | n-butyl | H | 3-chloropyridin-4-yl |

C. ANALYTICAL PART

For LCMS-characterization of the compounds of the present invention, the following method was used.

LCMS—General Procedure

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS detector. The MS detector was configured with an electrospray ionization source. Nitrogen was used as the nebulizer gas. The source temperature was maintained at 140° C. Data acquisition was performed with MassLynx-Openlynx software.

Method 1: In addition to the general procedure: Reversed phase HPLC was carried out on an XDB-C18 cartridge (1.8 μm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

Method 2:

In addition to the general procedure: Reversed phase HPLC was carried out on a XDB-C18 cartridge (1.8 μm, 2.1×30 mm) from Agilent, with a flow rate of 1.0 ml/min, at 60° C. The gradient conditions used are: 90% A (0.5 g/l ammonium acetate solution), 10% B (mixture of Acetonitrile/Methanol, 1/1), to 100% B in 6.5 minutes, kept till 7 minutes and equilibrated to initial conditions at 7.5 minutes until 9.0 minutes. Injection volume 2 μl. Low-resolution mass spectra (ZQ detector; quadrupole) were acquired by scanning from 100 to 1000 in 1.0 second using a dwell time of 0.3 second. The capillary needle voltage was 3 kV. The cone voltage was 20 V and 50 V for positive ionization mode and 20 V for negative ionization mode.

Method 3:

In addition to general procedure B: Reversed phase HPLC was carried out on an ACE-C18 column (3.0 μm, 4.6×30 mm) from Advanced Chromatography Technologies, with a flow rate of 1.5 ml/min, at 40° C. The gradient conditions used are: 80% A (0.5 g/l ammonium acetate solution), 10% B (acetonitrile), 10% C (methanol) to 50% B and 50% C in 6.5 minutes, to 100% B at 7 minutes and equilibrated to initial conditions at 7.5 minutes until 9.0 minutes. Injection volume 5 High-resolution mass spectra (Time of Flight, TOF) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

Melting Point Determination

Melting point determinations were performed on a Mettler FP62 apparatus.

TABLE 2

Analytical data ($R_t$ means retention time in minutes; $(MH)^+$ means the protonated mass of the compound (free base).

| Comp. No. | melting point (° C.) | $(MH)^+$ | $R_t$ | LCMS method |
|---|---|---|---|---|
| 1 | 137 | 390 | 4.40 | 1 |
| 2 | 156.4 | n.d. | n.d. | 1 |
| 3 | 152.7 | n.d. | n.d. | 1 |
| 4 | 127.1 | 378 | 4.02 | 1 |
| 5 | 125.2 | 378 | 3.94 | 1 |
| 6 | 169.9 | 392 | 4.26 | 1 |
| 7 | 114 | 392 | 4.23 | 1 |
| 8 | decomposes | 390 | 3.99 | 1 |
| 9 | 201.2 | 390 | 3.97 | 1 |
| 10 | decomposes | 390 | 4.04 | 1 |
| 11 | decomposes | 390 | 4.06 | 1 |
| 12 | 104.8 | 378 | 4.00 | 1 |
| 13 | 110.7 | 390 | 3.99 | 1 |
| 14 | 145.8 | 390 | 3.89 | 2 |
| 15 | 172.2 | 396 | 4.10 | 1 |
| 16 | 136.7 | 360 | 3.96 | 1 |
| 17 | n.d. | 360 | 4.22 | 1 |
| 18 | 121 | 360 | 3.97 | 1 |
| 19 | n.d. | 378 | 4.00 | 3 |
| 20 | n.d. | 380 | 4.10 | 1 | n.d.: not determined

D. PHARMACOLOGICAL EXAMPLES

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of formula (I) are present. Compounds of formula (I) are expected to have their effect substantially at mGluR2 by virtue of their ability to enhance the function of the receptor. The behaviour of positive allosteric modulators tested at mGluR2 using the [$^{35}$S]GTPγS binding assay method described below and which is suitable for the identification of such compounds, and more particularly the compounds according to formula (I), are shown in Table 3.

[$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein γ subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. mGluR2 receptors are shown to be preferentially coupled to Gγi-protein, a preferential coupling for this method, and hence it is widely used to study receptor activation of mGluR2 receptors both in recombinant cell lines and in tissues (Schaffhauser et al 2003, Pinkerton et al, 2004, Mutel et al (1998) Journal of Neurochemistry. 71:2558-64; Schaffhauser et al (1998) Molecular Pharmacology 53:228-33). Here we describe the use of the [$^{35}$S]GTPγS binding assay using membranes from cells transfected with the human mGluR2 receptor and adapted from Schaffhauser et al ((2003) Molecular Pharmacology 4:798-810) for the detection of the positive allosteric modulation (PAM) properties of the compounds of this invention.

Membrane Preparation

CHO-cells were cultured to pre-confluence and stimulated with 5 mM butyrate for 24 hours, prior to washing in PBS, and then collection by scraping in homogenisation buffer (50 mM Tris-HCl buffer, pH 7.4, 4° C.). Cell lysates were homogenized briefly (15 s) using an ultra-turrax homogenizer. The homogenate was centrifuged at 23 500×g for 10 minutes and the supernatant discarded. The pellet was resuspended in 5 mM Tris-HCl, pH 7.4 and centrifuged again (30 000×g, 20 min, 4° C.). The final pellet was resuspended in 50 mM HEPES, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds in membranes containing human mGluR2 was performed using frozen membranes that were thawed and briefly homogenised prior to pre-incubation in 96-well microplates (15 μg/assay well, 30 minutes, 30° C.) in assay buffer (50 mM HEPES pH 7.4, 100 mM NaCl, 3 mM MgCl$_2$, 50 μM GDP, 10 μg/ml saponin,) with increasing concentrations of positive allosteric modulator (from 0.3 nM to 50 μM) and either a minimal pre-determined concentration of glutamate (PAM assay), or no added glutamate. For the PAM assay, membranes were pre-incubated with glutamate at EC$_{25}$ concentration, i.e. a concentration that gives 25% of the maximal response glutamate, and is in accordance to published data (Pin et al. (1999) Eur. J. Pharmacol. 375:277-294). After addition of [$^{35}$S]GTPγS (0.1 nM, f.c.) to achieve a total reaction volume of 200 μl, microplates were shaken briefly and further incubated to allow [$^{35}$S]GTPγS incorporation on activation (30 minutes, 30° C.). The reaction was stopped by rapid vacuum filtration over glass-fibre filter plates (Unifilter 96-well GF/B filter plates, Perkin-Elmer, Downers Grove, USA) microplate using a 96-well plate cell harvester (Filtermate, Perkin-Elmer, USA), and then by washing three times with 300 μl of ice-cold wash buffer (Na$_2$PO$_4$.2H$_2$O 10 mM, NaH$_2$PO$_4$.H$_2$O 10 mM, pH=7.4). Filters were then air-dried, and 40 μl of liquid scintillation cocktail (Microscint-O) was added to each well, and membrane-bound [$^{35}$S]GTPγS was measured in a 96-well scintillation plate reader (Top-Count, Perkin-Elmer, USA). Non-specific [$^{35}$S]GTPγS binding is determined in the presence of cold 10 μM GTP. Each curve was performed at least once using duplicate sample per data point and at 11 concentrations.

Data Analysis

The concentration-response curves of representative compounds of the present invention in the presence of added EC$_{25}$ of mGluR2 agonist glutamate to determine positive allosteric modulation (PAM), were generated using the Prism GraphPad software (Graph Pad Inc, San Diego, USA). The curves were fitted to a four-parameter logistic equation (Y=Bottom+(Top-Bottom)/(1+10^((LogEC$_{50}$−X)*Hill Slope) allowing determination of EC$_{50}$ values. The EC$_{50}$ is the concentration of a compound that causes a half-maximal potentiation of the glutamate response. This is calculated by subtracting the maximal responses of glutamate in presence of a fully saturating concentration of a positive allosteric modulator from the response of glutamate in absence of a positive allosteric modulator. The concentration producing the half-maximal effect is then calculated as EC$_{50}$.

TABLE 3

Pharmacological data for compounds according to the invention. All compounds were tested in presence of mGluR2 agonist, glutamate at a predetermined EC$_{25}$ concentration, to determine positive allosteric modulation (GTPγS-PAM). Values shown are averages of duplicate values of 11-concentration response curves, from at least one experiment. All tested compounds showed a pEC$_{50}$ (−logEC$_{50}$) value of more than 5.0. The error of determination of a pEC$_{50}$ value for a single experiment is estimated to be about 0.3 log-units.

| Comp. No. | GTPgS - hR2 PAM pEC$_{50}$ |
| --- | --- |
| 1 | 6.09 |
| 2 | 6.86 |
| 3 | 6.34 |
| 4 | 6.41 |
| 5 | 6.36 |
| 6 | 6.36 |
| 7 | 6.46 |
| 8 | 6.10 |
| 9 | 6.15 |
| 10 | 6.43 |
| 11 | 6.17 |
| 12 | 6.27 |
| 13 | 6.38 |
| 14 | 6.42 |
| 15 | 6.15 |
| 16 | 6.36 |
| 17 | 6.0 |
| 18 | 6.4 |
| 19 | 6.8 |
| 20 | 6.2 |

E. COMPOSITION EXAMPLES

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula

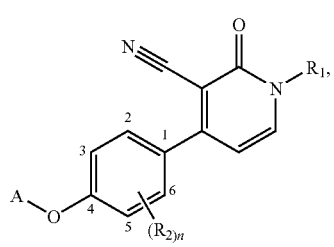

(I)

including any stereochemically isomeric form thereof, wherein $R_1$ is $C_{4-6}$alkyl, or $C_{1-3}$alkyl substituted with $C_{3-7}$cycloalkyl;

$R_2$ is hydrogen or halo;

A is pyridinyl substituted with one or two substituents, each substituent independently selected from halo or $C_{1-4}$alkyl;

n is an integer of value 1 or 2;

or a pharmaceutically acceptable salt thereof;

provided that if $R_2$ is 2-fluoro then A is not 3-pyridinyl substituted with one or two substituents, each substituent independently selected from halo or $C_{1-4}$alkyl, provided that a compound is not

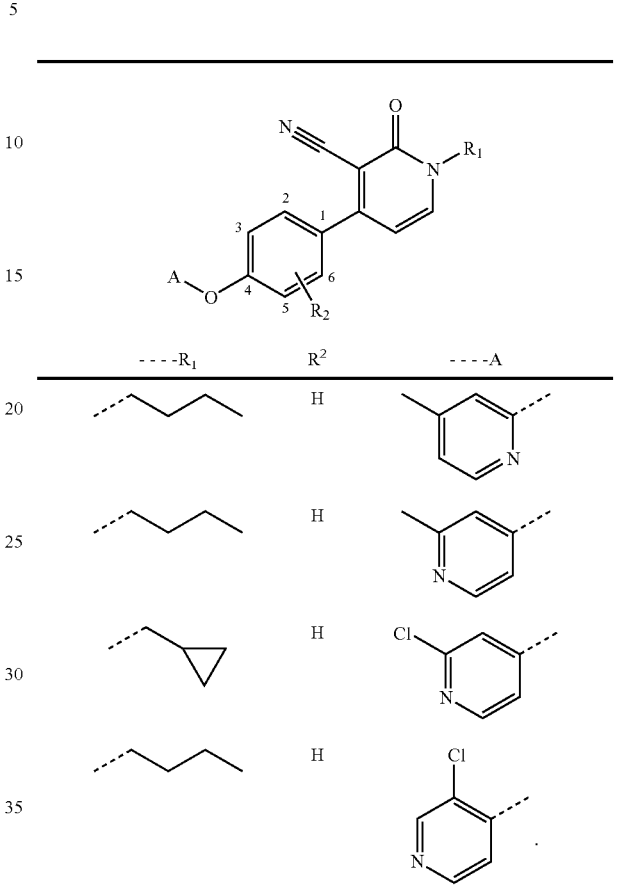

.

2. A compound as claimed in claim 1 wherein A is pyridinyl substituted with one substituent, wherein said substituent is halo or $C_{1-4}$ alkyl.

3. A compound as claimed in claim 1 wherein $R_1$ is $C_{4-6}$ alkyl.

4. A compound as claimed in claim 3 wherein $R_1$ is 1-butyl or 3-methyl-1-butyl.

5. A compound as claimed in claim 1 wherein $R_1$ is $C_{1-3}$ alkyl substituted with $C_{3-7}$ cycloalkyl.

6. A compound as claimed in claim 5 wherein $R_1$ is cyclopropylmethyl or 2-(cyclopropyl)-1-ethyl.

7. A compound as claimed in claim 1 wherein $R_2$ is hydrogen or fluoro.

8. A compound as claimed in claim 1 wherein $R_2$ is halo.

9. A compound as claimed in claim 8 wherein $R_2$ is fluoro.

10. A compound as claimed in claim 1 wherein n is 1 or 2 and $R_2$ is halo.

11. A compound as claimed in claim 1 wherein the pyridinyl ring represented by A is substituted with one substituent selected from chloro or methyl.

12. A compound as claimed in claim 1 wherein the pyridinyl ring represented by A is substituted with two substituents, each substituent independently being selected from chloro or methyl.

13. A compound as claimed in claim 1 wherein $R_1$ is 1-butyl, 3-methyl-1-butyl, cyclopropylmethyl or 2-(cyclopropyl)-1-ethyl; $R_2$ is hydrogen or fluoro; n is 1 or 2; A is pyridinyl substituted with one or two substituents, each substituent independently being selected from methyl or chloro.

14. A compound as claimed in claim 1 wherein the compound is selected from

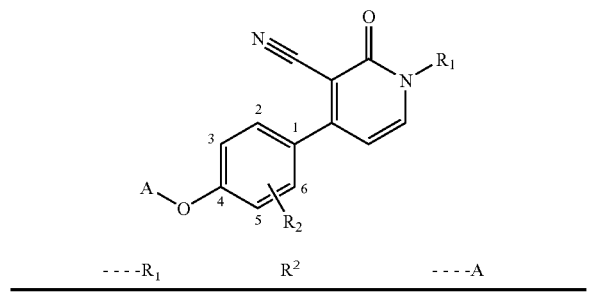

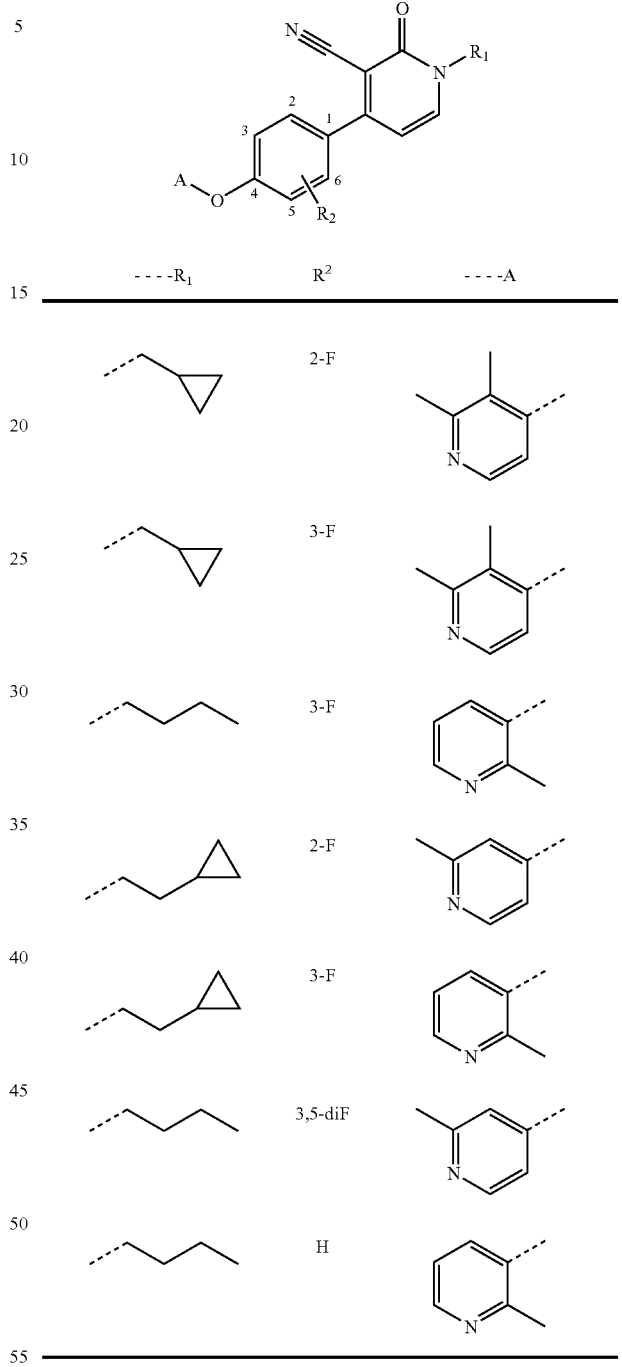

or a pharmaceutically acceptable salt thereof or a solvate thereof.

15. A pharmaceutical composition comprising a therapeutically effective amount of a compound as claimed in claim 1 and a pharmaceutically acceptable carrier or diluent.

16. A process for preparing a compound as claimed in claim 1, comprising reacting an intermediate of formula (II) wherein Y represents a group suitable for Pd mediated coupling with boronic acids or boronic esters, with an intermediate of formula (III) wherein $R_3$ and $R_4$ represent hydrogen or $C_{1-4}$alkyl; or wherein $R_3$ and $R_4$ may be taken together to form the bivalent radical of formula —$CH_2CH_2$—, —$CH_2CH_2CH_2$—, or —$C(CH_3)_2C(CH_3)_2$—, in a suitable reaction-inert solvent, in the presence of a suitable base and a suitable catalyst, under thermal conditions

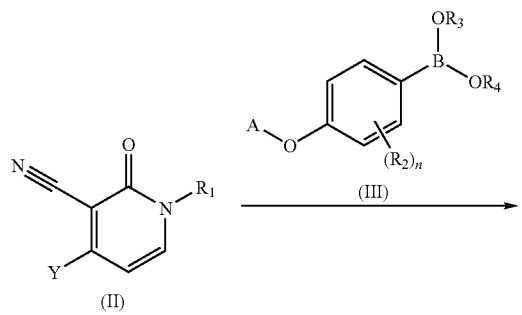

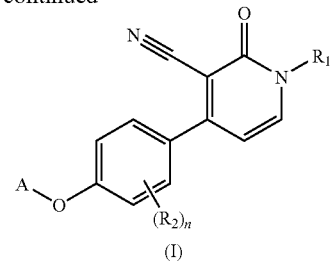

with $R_1$, $R_2$, A and n as defined in claim 1;

or, if desired, further converting compounds of formula (I) into each other following art-known transformations; or further, if desired, converting the compounds of formula (I), into a therapeutically active non-toxic acid addition salt by treatment with an acid, or conversely, converting the acid addition salt form into the free base by treatment with alkali; or, if desired, preparing stereochemically isomeric forms thereof.

\* \* \* \* \*